United States Patent
Day

(10) Patent No.: US 10,092,541 B2
(45) Date of Patent: *Oct. 9, 2018

(54) METHODS FOR THE TREATMENT OF DISEASES AMELIORATED BY PDE4 INHIBITION USING DOSAGE TITRATION OF APREMILAST

(71) Applicant: CELGENE CORPORATION, Summit, NJ (US)

(72) Inventor: Robert Day, Newtown, PA (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/826,027

(22) Filed: Aug. 13, 2015

(65) Prior Publication Data

US 2016/0045475 A1 Feb. 18, 2016

Related U.S. Application Data

(60) Provisional application No. 62/038,176, filed on Aug. 15, 2014.

(51) Int. Cl.

| | | |
|---|---|---|
| *A61K 31/4035* | (2006.01) | |
| *A61K 45/06* | (2006.01) | |
| *A61K 31/519* | (2006.01) | |
| *A61K 31/635* | (2006.01) | |
| *A61K 31/42* | (2006.01) | |
| *A61K 39/395* | (2006.01) | |
| *A61K 31/573* | (2006.01) | |
| *A61K 38/13* | (2006.01) | |
| *A61K 38/21* | (2006.01) | |

(52) U.S. Cl.
CPC .......... *A61K 31/4035* (2013.01); *A61K 31/42* (2013.01); *A61K 31/519* (2013.01); *A61K 31/573* (2013.01); *A61K 31/635* (2013.01); *A61K 38/13* (2013.01); *A61K 38/21* (2013.01); *A61K 39/3955* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 6,020,358 A | 2/2000 | Muller et al. | |
| 6,962,940 B2 | 11/2005 | Muller et al. | |
| 7,208,516 B2 | 4/2007 | Muller et al. | |
| 7,276,529 B2 | 10/2007 | Muller et al. | |
| 7,358,272 B2 | 4/2008 | Muller et al. | |
| 7,427,638 B2 | 9/2008 | Muller et al. | |
| 7,507,759 B2 | 3/2009 | Muller et al. | |
| 7,659,302 B2 | 2/2010 | Muller et al. | |
| 7,659,303 B2 | 2/2010 | Muller et al. | |
| 7,893,101 B2 | 2/2011 | Muller et al. | |
| 8,093,283 B2 | 1/2012 | Muller et al. | |
| 8,455,536 B2 * | 6/2013 | Muller | A61K 31/4035 514/417 |
| 8,629,173 B2 | 1/2014 | Muller et al. | |
| 2006/0148882 A1 | 7/2006 | Zeldis et al. | |
| 2006/0183787 A1 | 8/2006 | Muller et al. | |
| 2008/0234359 A1 | 9/2008 | Muller et al. | |
| 2009/0186923 A1 | 7/2009 | Armer et al. | |
| 2009/0239926 A1 | 11/2009 | Schafer et al. | |
| 2010/0168475 A1 | 7/2010 | Saindane et al. | |
| 2014/0024695 A1 | 1/2014 | Muller et al. | |
| 2014/0100259 A1 | 4/2014 | Muller et al. | |

FOREIGN PATENT DOCUMENTS

| | | |
|---|---|---|
| WO | WO 03/080049 A1 | 10/2003 |
| WO | WO 2006/065814 A1 | 6/2006 |
| WO | WO 2012/149251 A1 | 11/2012 |
| WO | WO 2014/151180 A1 | 9/2014 |

OTHER PUBLICATIONS

Papp et al. (The Lancet, 380(9843), 738-746, 2012).*
Schett et al. (Arthritis & Rheumatism, 64(10): 3156-03167, 2012).*
FDA label for Otezla® (apremilast) tablets (Mar. 2014).*
"Clinical Pharmacology Review NDA 205437 Apremilast Application No. 205437Orig1s000," Clinical Pharmacology and Biopharmaceutics Review(s), Nov. 21, 2013, Retrieved from the Internet: URL:http://www.accessdata.fda.gov/drugsatfda_docs/nda/2014/205437Orig1s000ClinPharmR.pdf, retrieved on Sep. 22, 2015, 114 pages.
Anonymous, "Highlights of prescribing information—Otezla," Mar. 1, 2014, Retrieved from the Internet: URL:http//web.archive.org/web/20140327021029/http://www.otezla.com/otezla-prescribing-information.pdf, retrieved on Sep. 22, 2015, 9 pages.

(Continued)

*Primary Examiner* — Bong-Sook Baek
(74) *Attorney, Agent, or Firm* — Jones Day

(57) ABSTRACT

Methods of treating, managing or preventing diseases ameliorated by inhibiting PDE4 such as psoriasis, ankylosing spondylitis, Behcet's disease, rheumatoid arthritis, atopic dermatitis, Crohn's disease, and ulcerative colitis are disclosed. Specific methods encompass the administration of apremilast in specific dosage titration schedule, alone or in combination with a second active agent.

24 Claims, No Drawings

(56) References Cited

OTHER PUBLICATIONS

Anonymous, "Oral Otezla® (apremilast) demostrated clinically meaningful and sustained improvements in skin, nail and scalp of adult patients with moderate to severe plaque psoriasis," Mar. 23, 2014, Retrieved from the Internet: URL:http://ir.celgene.com/releasedetail.cfm?releaseid=834900, retrieved on Sep. 22, 2015, pp. 1-6.

Baughman et al., "Release of tumor necrosis factor by alveolar macrophages of patients with sarcoidosis," *J. Lab. Clin. Med.* 115:36-42 (1990).

Beavo and Reifsnyder, "Primary sequence of cyclic nucleotide phosphodiesterase isozymes and the design of selective inhibitors," *Trends in Pharm.*, 11(4):150-155 (1990).

Bertolini et al., "Stimulation of bone resorption and inhibition of bone formation in vitro by human tumour necrosis factors," *Nature*, 319(6053):516-518 (1986).

Bissonnette et al., "Pulmonary inflammation and fibrosis in a murine model of asbestosis and silicosis. Possible role of tumor necrosis factor," *Inflammation* 13:329-339 (1989).

Carstensen, *Drug Stability: Principles & Practices*, Second Edition, Marcel Dekker, New York, NY, pp. 379-380 (1995).

Clouse et al., "Monokine regulation of human immunodeficiency virus-1 expression in a chronically infected human T cell clone," *J. Immunol.* 142:431-438 (1989).

Dezube et al., "Pentoxifylline and wellbeing in patients with cancer," Lancet, 335(8690):662 (1990).

Duh et al., "Tumor necrosis factor alpha activates human immunodeficiency virus type 1 through induction of nuclear factor binding to the NF-kappa B sites in the long terminal repeat," *Proc. Nat. Acad. Sci. USA*, 86:5974-5978 (1989).

Elliot et al., "TNF alpha blockade in rheumatoid arthritis: rationale, clinical outcomes and mechanisms of action," *Int. J. Immunopharmacol.*, 17:141-145 (1995).

Ferrari-Baliviera et al., "Tumor necrosis factor induces adult respiratory distress syndrome in rats," *Arch. Surg.*, 124(12):1400-1405 (1989).

Folks et al., "Tumor necrosis factor alpha induces expression of human immunodeficiency virus in a chronically infected T-cell clone," *Proc. Natl. Acad. Sci. USA*, 86(7):2365-2368 (1989).

Gottlieb et al., "Efficacy, tolerability, and pharmacodynamics of apremilast in recalcitrant plaque psoriasis: a phase II open-label study," *J. Drugs Dermatology*,12(8):888-897 (2013).

Grau et al., "Tumor necrosis factor and disease severity in children with falciparum malaria," *N. Engl. J. Med.*, 320(24):1586-1591 (1989).

Hinshaw et al., "Survival of primates in LD100 septic shock following therapy with antibody to tumor necrosis factor (TNF alpha)," *Circ. Shock* 30:279-292 (1990).

Holler et al., "Increased serum levels of tumor necrosis factor alpha precede major complications of bone marrow transplantation," *Blood*, 75(4):1011-1016 (1990).

Johnson et al., "Tumors producing human tumor necrosis factor induced hypercalcemia and osteoclastic bone resorption in nude mice," *Endocrinology* 124:1424-1427 (1989).

Kavanaugh et al., "Treatment of psoriatic arthritis in a phase 3 randomised, placebo-controlled trial with apremilast, an oral phosphodiesterase 4 inhibitor," *Ann. Rhuem. Dis.*, 73:1020-1026 (2014).

Lowe et al., Drugs of the Future, 17(9):799-807 (1992).

Lowe, "Tumour necrosis factor-α antagonists and their therapeutic applications," *Exp. Opin. Ther. Patents*, 8:1309-1322 (1998).

Millar et al., "Tumour necrosis factor in bronchopulmonary secretions of patients with adult respiratory distress syndrome," Lancet, 2(8665):712-714 (1989).

Monte et al., "Productive human immunodeficiency virus-1 infection of megakaryocytic cells is enhanced by tumor necrosis factor-alpha," *Blood* 79:2670-2679 (1992).

Nikolov, "Application No. 205437Orig1s000 Cross discipline team leader review," Center for Drug Evaluation and Research, Feb. 6, 2014, Retrieved from the Internet: URL:http://www.accessdata.fda.gov/drugsatfda_docs/nda/2014/205437Orig1s000CrossR.pdf, retrieved on Sep. 24, 2015, 42 pages.

Papp et al., "Efficacy of apremilast in the treatment of moderate to severe psoriasis: a randomised controlled trial," Lancet, 380:738-746 (2012).

Piguet et al., "Requirement of tumour necrosis factor for development of silica-induced pulmonary fibrosis," *Nature*, 344:245-247 (1990).

Poli et al., "The effect of cytokines and pharmacologic agents on chronic HIV infection," *AIDS Res. Hum. Retrovirus.*, 8(2):191-197 (1992).

Poli et al., "Tumor necrosis factor alpha functions in an autocrine manner in the induction of human immunodeficiency virus expression," *Proc. Nat. Acad. Sci. USA*, 87(2):782-785 (1990).

*The Merck Manual*, $17^{th}$ Edition, Merck & Company, West Point, PA, pp. 448, 944-952 (1999).

Tracey et al., "Anti-cachectin/TNF monoclonal antibodies prevent septic shock during lethal bacteraemia," *Nature*, 330(6149):662-664 (1987).

Van Dullemen et al., "Treatment of Crohn's disease with anti-tumor necrosis factor chimeric monoclonal antibody (cA2)," *Gastroenterology*, 109:129-135 (1995).

Verghese et al., "Differential regulation of human monocyte-derived TNF alpha and IL-1 beta by type IV cAMP-phosphodiesterase (cAMP-PDE) inhibitors," *J. Pharmacol. Exp. Ther.*, 272(3), 1313-1320 (1995).

Wolff ed., Burger's Medicinal Chemistry and Drug Discovery, 5th Edition, John Wiley & Sons, Inc., pp. 172-178, 949-982 (1995).

U.S. Appl. No. 60/366,515, filed Mar. 20, 2002, Schafer et al.

U.S. Appl. No. 60/438,450, filed Jan. 7, 2003, Schafer et al.

U.S. Appl. No. 60/634,982, filed Dec. 13, 2004, Zeldis et al.

Anonymous, "A Phase 3, Multicenter, Randomized, Double-Blind, Placebo-Controlled, Parallel-Group, Efficacy and Safety Study of Two Doses of Apremilast (CC-10004) in Subjects With Active Psoriatic Arthritis Who Have Not Been Previously Treated With Disease Modifying Anti-rheumatic Drugs," retrieved from http://clinicaltrials.gov/archive/NCT01307423/2012_09_06 on May 22, 2014.

STN File CA, Registry No. 608141-41-9, entered STN on Oct. 23, 2003, Chemical Abstracts Index Name "Acetamide, N-[2-[(1S)-1-(3-ethoxy-4-methoxyphenyl)-2-(methylsulfonyl)ethyl]-2,3-dihydro-1,3-dioxo-1H-isoindol-4-yl]".

Dong et al., "Inhibition of PDE3, PDE4 and PDE7 potentiates glucocorticoid-induced apoptosis and overcomes glucocorticoid resistance in CEM T leukemic cells," Biochem. Pharmacol., 79(3):321-329 (2010).

Fox et al., "Combined oral cyclosporin and methotrexate therapy in patients with rheumatoid arthritis elevates methotrexate levels and reduces 7-hydroxymethotrexate levels when compared with methotrexate alone," Rheumatology (Oxford), 42(8):989-994 (2003).

Gladman et al., Kelley's Textbook of Rheumatology, 2 vols. 6th Edition, W. B. Saunders Company, Chapter 71, pp. 1071-1077 (2001).

Gladman, "Current concepts in psoriatic arthritis," Curr. Opin. Rheumatol., 14(4):361-366 (2002).

Kowalczyk et al., "Effect of phosphodiesterase antagonists on glucocorticoid mediated growth inhibition in murine skin cell lines," Eur. J. Pharmacol., 610(1-3):29-36 (2009).

Long et al., "Human articular chondrocytes produce IL-7 and respond to IL-7 with increased production of matrix metalloproteinase-13," Arthritis Res. Ther., 10(1):R23 (2008).

McCann et al., "Apremilast, a novel PDE4 inhibitor, inhibits spontaneous production of tumour necrosis factor-alpha from human rheumatoid synovial cells and ameliorates experimental arthritis," Arthritis Res. Ther., 12(3):R107 (2010).

Meyers et al., "Phosphodiesterase 4 inhibitors augment levels of glucocorticoid receptor in B cell chronic lymphocytic leukemia but not in normal circulating hematopoietic cells," Clin. Cancer Res., 13(16):4920-4927 (2007).

Patel et al., "Psoriatic arthritis—emerging concepts," Rheumatology (Oxford), 40(3):243-246 (2001).

(56) References Cited

OTHER PUBLICATIONS

Rihl et al., "Identification of interleukin-7 as a candidate disease mediator in spondylarthritis," Arthritis Rheum., 58(11):3430-3435 (2008).
Tierney et al. (eds), Current Medical Diagnosis & Treatment 1998, 37th Edition, Appleton & Lange, Stamford, CT, p. 793 (1998).
Wilen et al., "Strategies in optical resolutions," Tetrahedron, 33:2725-2736 (1977).
Wilen, Tables of Resolving Agents and Optical Resolutions, (E.L. Eliel, Ed.), University of Notre Dame Press, Notre Dame, IN, p. 268 (1972).

* cited by examiner

METHODS FOR THE TREATMENT OF DISEASES AMELIORATED BY PDE4 INHIBITION USING DOSAGE TITRATION OF APREMILAST

This application claims priority to U.S. Provisional Patent Application No. 62/038,176, filed Aug. 15, 2014, the entirety of which is incorporated herein by reference.

1. FIELD

Provided herein are methods for treating, preventing and/or managing diseases ameliorated by PDE4 inhibition such as psoriasis, ankylosing spondylitis, Behcet's disease, rheumatoid arthritis, atopic dermatitis, Crohn's disease, and ulcerative colitis by administering apremilast in a specific dosage titration schedule. Also provided herein are pharmaceutical compositions and dosage forms comprising specific amounts of apremilast suitable for use in methods of treating, preventing and/or managing psoriasis, ankylosing spondylitis, Behcet's disease, rheumatoid arthritis, atopic dermatitis, Crohn's disease, and ulcerative colitis. The compounds disclosed herein are for use in the methods of the invention.

2. BACKGROUND

Adenosine 3',5'-cyclic monophosphate (cAMP) plays a role in many diseases and conditions, such as but not limited to inflammation, and other conditions (Lowe and Cheng, *Drugs of the Future*, 17(9), 799-807, 1992). It has been shown that the elevation of cAMP in inflammatory leukocytes inhibits their activation and the subsequent release of inflammatory mediators, including TNF-α and NF-κB.

It is believed that the primary cellular mechanism for the inactivation of cAMP is the breakdown of cAMP by a family of isoenzymes referred to as cyclic nucleotide phosphodiesterases (PDE) (Beavo and Reitsnyder, *Trends in Pharm.*, 11, 150-155, 1990). It is recognized, for example, that the inhibition of PDE type IV is particularly effective in the inhibition of inflammatory mediator release (Verghese, et al., *Journal of Pharmacology and Experimental Therapeutics*, 272(3), 1313-1320, 1995). Thus, compounds that inhibit PDE4 (PDE IV) specifically may inhibit inflammation with a minimum of unwanted side effects such as cardiovascular or anti-platelet effects.

Inflammatory diseases such as arthritis, related arthritic conditions (e.g., ankylosing spondylitis, osteoarthritis and rheumatoid arthritis), Behcet's disease, inflammatory bowel disease (e.g., Crohn's disease and ulcerative colitis), psoriasis, atopic dermatitis and contact dermatitis are prevalent and problematic ailments. TNF-α plays a central role in the inflammatory response and the administration of their antagonists block chronic and acute responses in animal models of inflammatory disease. Enhanced or unregulated TNF-α production has been implicated in a number of diseases, for example psoriasis, ankylosing spondylitis, Behcet's disease, rheumatoid arthritis, atopic dermatitis, Crohn's disease, and ulcerative colitis. Tracey et al., 1987, *Nature* 330:662-664 and Hinshaw et al., 1990, *Circ. Shock* 30:279-292 (endotoxic shock); Dezube et al., 1990, *Lancet*, 335:662 (cachexia); Millar et al., 1989, *Lancet* 2:712-714 and Ferrai-Baliviera et al., 1989, *Arch. Surg.* 124:1400-1405 (adult respiratory distress syndrome); Bertolini et al., 1986, *Nature* 319:516-518, Johnson et al., 1989, *Endocrinology* 124:1424-1427, Holler et al., 1990, *Blood* 75:1011-1016, and Grau et al., 1989, *N. Engl. J. Med.* 320:1586-1591 (bone resorption diseases); Pignet et al., 1990, *Nature*, 344:245-247, Bissonnette et al., 1989, *Inflammation* 13:329-339 and Baughman et al., 1990, *J. Lab. Clin. Med.* 115:36-42 (chronic pulmonary inflammatory diseases); Elliot et al., 1995, *Int. J. Pharmac.* 17:141-145 (rheumatoid arthritis); von Dullemen et al., 1995, *Gastroenterology*, 109:129-135 (Crohn's disease); Duh et al., 1989, *Proc. Nat. Acad. Sci.* 86:5974-5978, Poll et al., 1990, *Proc. Nat. Acad. Sci.* 87:782-785, Monto et al., 1990, *Blood* 79:2670, Clouse et al., 1989, *J. Immunol.* 142, 431-438, Poll et al., 1992, *AIDS Res. Hum. Retrovirus*, 191-197, Poli et al. 1990, *Proc. Natl. Acad. Sci.* 87:782-784, Folks et al., 1989, *PNAS* 86:2365-2368 (HIV and opportunistic infections resulting from HIV).

Therefore, pharmaceutical compounds that can inhibit PDE4 or TNF-α, may be beneficial therapeutics. Small-molecule inhibitors have demonstrated an ability to treat or prevent inflammatory diseases implicated by PDE4 or TNF-α (for a review, see Lowe, 1998 *Exp. Opin. Ther. Patents* 8:1309-1332). One such class of molecules is the substituted phenethylsulfones described in U.S. Pat. No. 6,020,358.

There is a significant need for safe and effective methods of treating, preventing and managing psoriasis, ankylosing spondylitis, Behcet's disease, rheumatoid arthritis, atopic dermatitis, Crohn's disease, and ulcerative colitis, particularly for patients that are refractory to conventional treatments. In addition, there is a need to treat such disease while reducing or avoiding the toxicity and/or side effects associated with conventional therapies.

3. SUMMARY

Provided herein are methods of treating, preventing and/or managing psoriasis, ankylosing spondylitis, Behcet's disease, rheumatoid arthritis, atopic dermatitis, Crohn's disease, and ulcerative colitis in humans in need thereof using specific dosage titration schedule of apremilast. The methods comprise administering to a patient in need of such treatment, prevention or management a therapeutically or prophylactically effective amount of apremilast, or a pharmaceutically acceptable prodrug, metabolite, polymorph, salt, solvate (e.g., hydrate) or clathrate thereof in specific dosage titration schedule.

In some embodiments, provided herein are methods of treating psoriasis, ankylosing spondylitis, Behcet's disease, rheumatoid arthritis, atopic dermatitis, Crohn's disease, and ulcerative colitis, which comprises orally administering to a patient having psoriasis, ankylosing spondylitis, Behcet's disease, rheumatoid arthritis, atopic dermatitis, Crohn's disease, or ulcerative colitis escalating doses of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof, wherein a starting dose is between about 10 mg/day and about 20 mg/day, and a maximum dose is between about 40 mg/day and about 100 mg/day.

In some embodiments, the method comprises the following initial titration schedule:
(i) 10 mg in the morning on the first day of administration;
(ii) 10 mg in the morning and 10 mg after noon on the second day of administration;
(iii) 10 mg in the morning and 20 mg after noon on the third day of administration;
(iv) 20 mg in the morning and 20 mg after noon on the fourth day of administration;
(v) 20 mg in the morning and 30 mg after noon on the fifth day of administration; and (vi) 30 mg in the morning and 30 mg after noon on the sixth and every subsequent day of administration.

In some embodiments, the methods further comprise the administration of a therapeutically or prophylactically effective amount of at least a second active agent, including but not limited to, an anti-inflammatory agent, an immunosuppressant, mycophenolate mofetil, a biologic agent, or a Cox-2 inhibitor.

In another embodiment, apremilast, or a pharmaceutically acceptable prodrug, metabolite, polymorph, salt, solvate (e.g., hydrate) or clathrate thereof is administered orally in a dosage form such as a tablet and a capsule.

4. DETAILED DESCRIPTION

4.1 Definitions

As used herein, the term "apremilast" refers to (+)-2-[1-(3-ethoxy-4-methoxyphenyl)-2-methylsulfonylethyl]-4-acetylaminoisoindoline-1,3-dione, also known as N-[2-[(1S)-1-(3-ethoxy-4-methoxylphenyl)-2-(methylsulfonyl)ethyl]-2,3-dihydro-1,3-dioxo-1H-isoindol-4-yl]acetamide. Apremilast has the following structure:

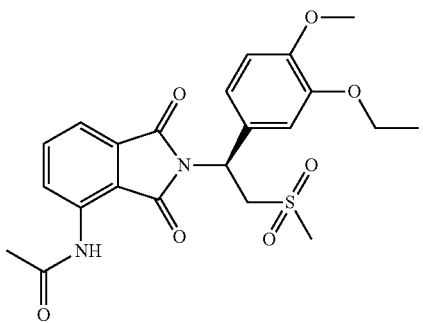 [SMILES: CCOc1cc([C@@H](CS(C)(=O)=O)N2C(=O)c3cccc(NC(C)=O)c3C2=O)ccc1OC]

As used herein and unless otherwise indicated, the term "pharmaceutically acceptable salt" includes, but is not limited to, salts prepared from pharmaceutically acceptable non-toxic acids or bases including inorganic acids and bases and organic acids and bases. Suitable pharmaceutically acceptable base addition salts provided herein include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts.

As used herein and unless otherwise indicated, the term "hydrate" means a compound provided herein or a salt thereof that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., monohydrate, dihydrate, trihydrate, tetrahydrate and the like).

As used herein and unless otherwise indicated, the term "polymorph" means solid crystalline forms of a compound provided herein or complex thereof. Different polymorphs of the same compound can exhibit different physical, chemical and/or spectroscopic properties.

As used herein and unless otherwise specified, the term "prodrug" means a derivative of a compound that can hydrolyze, oxidize, or otherwise react under biological conditions (in vitro or in vivo) to provide the compound. Examples of prodrugs include, but are not limited to, derivatives and metabolites of apremilast that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by 1 *Burger's Medicinal Chemistry and Drug Discovery*, 172-178, 949-982 (Manfred E. Wolff ed., 5th ed. 1995).

As used herein, and unless otherwise specified, the term "enantiomer," "isomer" or "stereoisomer" encompasses all enantiomerically/stereomerically pure and enantiomerically/stereomerically enriched compounds provided herein.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure, when the compound contains greater than or equal to 80%, 90%, 95%, 96%, 97%, 98% or 99% of one stereoisomer, and 20%, 10%, 5%, 4%, 3%, 2%, 1% or less of the counter stereoisomer. "Substantially free of its (R) enantiomer" is encompassed by the term stereomerically pure or enantiomerically pure.

As used herein, term "adverse effect" includes, but is not limited to gastrointestinal, renal and hepatic toxicities, leukopenia, increases in bleeding times due to, e.g., thrombocytopenia, and prolongation of gestation, nausea, vomiting, somnolence, asthenia, dizziness, teratogenicity, extra-pyramidal symptoms, akathisia, cardiotoxicity including cardiovascular disturbances, inflammation, male sexual dysfunction, and elevated serum liver enzyme levels. The term "gastrointestinal toxicities" includes but is not limited to gastric and intestinal ulcerations and erosions. The term "renal toxicities" includes but is not limited to such conditions as papillary necrosis and chronic interstitial nephritis.

As used herein, the term "patient" refers to a mammal, particularly a human. In some embodiments, the patient is a female. In further embodiments, the patient is a male. In further embodiments, the patient is a pediatric (a newborn, an infant, a child, or an adolescent).

As used herein, and unless otherwise specified, the term "pediatrics" or "pediatric medicine" refers to the branch of medicine that deals with the medical care of newborns, infants, children, and adolescents. The approximate age range of a newborn is from birth to 1 month of age. The approximate age range of an infant is greater than 1 month to 2 years of age. The approximate age range of a child is greater than 2 years to 12 years of age. The approximate age range of an adolescent is greater than 12 years to 21 years of age.

As used herein, and unless otherwise specified, the terms "treat," "treating" and "treatment" contemplate an action that occurs while a patient is suffering from the specified disease or disorder, which reduces the severity or symptoms of the disease or disorder, or retards or slows the progression or symptoms of the disease or disorder.

As used herein, unless otherwise specified, the terms "prevent," "preventing" and "prevention" contemplate an action that occurs before a patient begins to suffer from the specified disease or disorder, which inhibits or reduces the severity or symptoms of the disease or disorder.

As used herein, and unless otherwise indicated, the terms "manage," "managing," and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

4.2 Methods of Treatment and Prevention

Provided herein are methods of treating, managing and/or preventing psoriasis, ankylosing spondylitis, Behcet's disease, rheumatoid arthritis, atopic dermatitis, Crohn's disease, and ulcerative colitis, which comprise administering to a patient in need of such treatment, management or prevention a therapeutically or prophylactically effective amount of apremilast, or a pharmaceutically acceptable prodrug, metabolite, polymorph, salt, solvate or clathrate thereof in a specific dosage titration schedule. Apremilast, or a pharmaceutically acceptable prodrug, metabolite, polymorph, salt, solvate or clathrate thereof, is provided for use in the methods of treatment, management and/or prevention disclosed herein.

Provided herein are methods of treating psoriasis, which comprise administering to a patient in need of such treatment a therapeutically effective amount of apremilast, or a pharmaceutically acceptable prodrug, metabolite, polymorph, salt, solvate or clathrate thereof in a specific dosage titration schedule.

Provided herein are methods of treating ankylosing spondylitis, which comprise administering to a patient in need of such treatment a therapeutically effective amount of apremilast, or a pharmaceutically acceptable prodrug, metabolite, polymorph, salt, solvate or clathrate thereof in a specific dosage titration schedule.

Provided herein are methods of treating Behcet's disease, which comprise administering to a patient in need of such treatment a therapeutically effective amount of apremilast, or a pharmaceutically acceptable prodrug, metabolite, polymorph, salt, solvate or clathrate thereof in a specific dosage titration schedule.

Provided herein are methods of treating rheumatoid arthritis, which comprise administering to a patient in need of such treatment a therapeutically effective amount of apremilast, or a pharmaceutically acceptable prodrug, metabolite, polymorph, salt, solvate or clathrate thereof in a specific dosage titration schedule.

Provided herein are methods of treating atopic dermatitis, which comprise administering to a patient in need of such treatment a therapeutically effective amount of apremilast, or a pharmaceutically acceptable prodrug, metabolite, polymorph, salt, solvate or clathrate thereof in a specific dosage titration schedule.

Provided herein are methods of treating Crohn's disease, which comprise administering to a patient in need of such treatment a therapeutically effective amount of apremilast, or a pharmaceutically acceptable prodrug, metabolite, polymorph, salt, solvate or clathrate thereof in a specific dosage titration schedule.

Provided herein are methods of treating ulcerative colitis, which comprise administering to a patient in need of such treatment a therapeutically effective amount of apremilast, or a pharmaceutically acceptable prodrug, metabolite, polymorph, salt, solvate or clathrate thereof in a specific dosage titration schedule.

Apremislast is provided for use in the methods of treatment of the invention.

In some embodiments apremilast is provided for use in the methods of treatment, management and/or prevention of a disease disclosed herein.

In some embodiments the disease is psoriasis. In some embodiments the disease is ankylosing spondylitis. In some embodiments the disease is Behcet's disease. In some embodiments the disease is rheumatoid arthritis. In some embodiments the disease is atopic dermatitis. In some embodiments the disease is Crohn's disease. In some embodiments the disease is ulcerative colitis.

In some embodiments apremilast is present as a pharmaceutically acceptable prodrug thereof. In some embodiments apremilast is present as a pharmaceutically acceptable metabolite thereof. In some embodiments apremilast is present as a pharmaceutically acceptable polymorph thereof. In some embodiments apremilast is present as a pharmaceutically acceptable salt thereof. In some embodiments apremilast is present as a pharmaceutically acceptable solvate thereof. In some embodiments apremilast is present as a pharmaceutically acceptable clathrate thereof.

In some embodiments, the methods also encompass inhibiting or averting signs and symptoms of psoriasis, ankylosing spondylitis, Behcet's disease, rheumatoid arthritis, atopic dermatitis, Crohn's disease, or ulcerative colitis as well as addressing the disease itself, prior to the onset of symptoms by administering apremilast, or a pharmaceutically acceptable prodrug, metabolite, polymorph, salt, solvate or clathrate thereof in a specific dosage titration schedule. Patients having history of psoriasis, ankylosing spondylitis, Behcet's disease, rheumatoid arthritis, atopic dermatitis, Crohn's disease, or ulcerative colitis are preferred candidates for preventive regimens. In some embodiments, apremilast, or a pharmaceutically acceptable prodrug, metabolite, polymorph, salt, solvate or clathrate thereof is provided for use in the methods of inhibiting or averting signs and symptoms of psoriasis, ankylosing spondylitis, Behcet's disease, rheumatoid arthritis, atopic dermatitis, Crohn's disease, or ulcerative colitis as well as addressing the disease itself, prior to the onset of symptoms.

In certain embodiments, apremilast is orally administered to a patient having psoriasis, ankylosing spondylitis, Behcet's disease, rheumatoid arthritis, atopic dermatitis, Crohn's disease, or ulcerative colitis in a twice daily dose of 30 mg per day (i.e., 60 mg per day). In certain embodiments, apremilast is for use in the methods of oral administration.

In some embodiments, the patient is an adult.
In some embodiments, the patient is a newborn.
In some embodiments, the patient is an infant.
In some embodiments, the patient is a child.
In some embodiments, the patient is an adolescent.

In some embodiments, provided herein are methods of treating psoriasis, ankylosing spondylitis, Behcet's disease, rheumatoid arthritis, atopic dermatitis, Crohn's disease, and ulcerative colitis, which comprises orally administering to a patient having psoriasis, ankylosing spondylitis, Behcet's disease, rheumatoid arthritis, atopic dermatitis, Crohn's disease, or ulcerative colitis escalating doses of stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof, wherein a starting dose is between about 10 mg/day and about 20 mg/day, and a maximum dose is between about 40 mg/day and about 100 mg/day. Stereomerically pure (+)-2-[1-(3-ethoxy-4-methoxyphenyl)-2-methylsulfonylethyl]-4-acetylaminoisoindoline-1,3-dione, or a pharmaceutically acceptable prodrug, polymorph, salt, or solvate thereof, is provided for use in the methods of treatment disclosed herein above.

In some embodiments, the method comprises the following initial titration schedule:
(i) 10 mg in the morning on the first day of administration;
(ii) 10 mg in the morning and 10 mg after noon on the second day of administration;
(iii) 10 mg in the morning and 20 mg after noon on the third day of administration;
(iv) 20 mg in the morning and 20 mg after noon on the fourth day of administration;
(v) 20 mg in the morning and 30 mg after noon on the fifth day of administration; and
(vi) 30 mg in the morning and 30 mg after noon on the sixth and every subsequent day of administration.

In some embodiments, the dosing schedule may be represented as follows:

| Day 1 | Day 2 | | Day 3 | | Day 4 | | Day 5 | | Day 6 & thereafter | |
| --- | --- | --- | --- | --- | --- | --- | --- | --- | --- | --- |
| AM | AM | PM | AM | PM | AM | PM | AM | PM | AM | PM |
| 10 mg | 10 mg | 10 mg | 10 mg | 20 mg | 20 mg | 20 mg | 20 mg | 30 mg | 30 mg | 30 mg |

In some embodiments, the method comprises the following initial titration schedule:
(i) 10 mg in the morning on the first day of administration;
(ii) 10 mg in the morning and 10 mg after noon on the second day of administration;
(iii) 10 mg in the morning and 20 mg after noon on the third day of administration;
(iv) 20 mg in the morning and 20 mg after noon on the fourth day of administration;
(v) 20 mg in the morning and 30 mg after noon on the fifth day of administration;
(vi) 30 mg in the morning and 30 mg after noon on the sixth day of administration;
(vii) 30 mg in the morning and 40 mg after noon on the seventh day of administration;
(viii) 40 mg in the morning and 40 mg after noon on the eighth and every subsequent day of administration.

In some embodiments, the method comprises the following initial titration schedule:
(i) 10 mg in the morning on the first day of administration;
(ii) 10 mg in the morning and 10 mg after noon on the second day of administration;
(iii) 10 mg in the morning and 20 mg after noon on the third day of administration;
(iv) 20 mg in the morning and 20 mg after noon on the fourth and every subsequent day of administration.

In some embodiments, the method comprises the following initial titration schedule:
(i) 10 mg in the morning and 10 mg after noon on the first and second day of administration;
(ii) 20 mg in the morning and 20 mg after noon on the third and fourth day of administration;
(iii) 30 mg in the morning and 30 mg after noon on the fifth and every subsequent day of administration.

In one embodiment, stereomerically pure apremilast, (+)-2-[1-(3-ethoxy-4-methoxyphenyl)-2-methylsulfonylethyl]-4-acetylaminoisoindoline-1,3-dione, is administered according the above schedule. In one embodiment, stereomerically pure apremilast, (+)-2-[1-(3-ethoxy-4-methoxyphenyl)-2-methylsulfonylethyl]-4-acetylaminoisoindoline-1,3-dione is provided for use in methods of administration according to the above schedules.

In one embodiment, the dosage of apremilast, (+)-2-[1-(3-ethoxy-4-methoxyphenyl)-2-methylsulfonylethyl]-4-acetylaminoisoindoline-1,3-dione, may be reduced to 30 mg once daily in patients with severe renal impairment.

In one embodiment, apremilast, (+)-2-[1-(3-ethoxy-4-methoxyphenyl)-2-methylsulfonylethyl]-4-acetylaminoisoindoline-1,3-dione, can be administered without regard to meals according the above schedule.

In some embodiments, the stereomerically pure (+)-2-[1-(3-ethoxy-4-methoxyphenyl)-2-methylsulfonylethyl]-4-acetylaminoisoindoline-1,3-dione comprises greater than about 90% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 95% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 96% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 97% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 98% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione comprises greater than about 99% by weight of (+) isomer based on the total weight percent of the compound.

In some embodiments, the stereomerically pure (+)-2-[1-(3-ethoxy-4-methoxyphenyl)-2-methylsulfonylethyl]-4-acetylaminoisoindoline-1,3-dione is administered in an amount of about 20 mg twice a day following the initial titration schedule.

In some embodiments, the stereomerically pure (+)-2-[1-(3-ethoxy-4-methoxyphenyl)-2-methylsulfonylethyl]-4- acetylaminoisoindoline-1,3-dione is administered in an amount of about 30 mg twice a day following the initial titration schedule.

In some embodiments, the stereomerically pure (+)-2-[1-(3-ethoxy-4-methoxyphenyl)-2-methylsulfonylethyl]-4-acetylaminoisoindoline-1,3-dione is administered once or twice daily.

In some embodiments, the stereomerically pure (+)-2-[1-(3-ethoxy-4-methoxyphenyl)-2-methylsulfonylethyl]-4-acetylaminoisoindoline-1,3-dione is administered in tablet form. In some embodiments, the tablet comprises a 10 mg, 20 mg or 30 mg dose of stereomerically pure (+)-2-[1-(3-ethoxy-4-methoxyphenyl)-2-methylsulfonylethyl]-4-acetylaminoisoindoline-1,3-dione.

In some embodiments, the methods provided herein, further comprise administering to the patient a therapeutically effective amount of a second active agent. In some embodiments, the second active agent is an anti-inflammatory agent, an immunosuppressant, mycophenolate mofetil, a biologic agent, or a Cox-2 inhibitor. In some embodiments, the second active agent is a nonsteroidal anti-inflammatory agent. In some embodiments, the second active agent is a disease-modifying anti-rheumatic agent. In some embodiments, the second active agent is methotrexate. In some embodiments, the second active agent is sulfasalazine. In some embodiments, the second active agent is leflunomide. In some embodiments, the second active agent is etanercept. In some embodiments, the second active agent is an oral corticosteroid. In some embodiments, the second active agent is prednisone. In some embodiments, a second active agent is provided for administration in the methods disclosed herein.

In some embodiments, the patient has received prior treatment for psoriasis, ankylosing spondylitis, Behcet's disease, rheumatoid arthritis, atopic dermatitis, Crohn's disease, or ulcerative colitis. In some embodiments, the prior treatment is with a disease-modifying antirheumatic drug. In some embodiments, the psoriasis, ankylosing spondylitis, Behcet's disease, rheumatoid arthritis, atopic dermatitis, Crohn's disease, or ulcerative colitis is refractory to the prior treatment.

In some embodiments, the method comprises administering stereomerically pure (+)-2-[1-(3-ethoxy-4-methoxyphenyl)-2-methylsulfonylethyl]-4-acetylaminoisoindoline-1,3-dione, substantially free of any salt, solvate, or prodrug forms of (+)-2-[1-(3-ethoxy-4-methoxyphenyl)-2-methylsulfonylethyl]-4-acetylaminoisoindoline-1,3-dione.

In some embodiments, the method comprises administering a pharmaceutically acceptable salt of stereomerically pure (+)-2-[1-(3-ethoxy-4-methoxyphenyl)-2-methylsulfonylethyl]-4-acetylaminoisoindoline-1,3-dione.

In some embodiments, the method comprises administering a pharmaceutically acceptable solvate of stereomerically pure (+)-2-[1-(3-ethoxy-4-methoxyphenyl)-2-methylsulfonylethyl]-4-acetylaminoisoindoline-1,3-dione.

4.2.1 Combination Therapy

In particular methods encompassed by this embodiment, apremilast is administered in combination with another drug ("second active agent") for treating, managing and/or preventing psoriasis, ankylosing spondylitis, Behcet's disease, rheumatoid arthritis, atopic dermatitis, Crohn's disease, or ulcerative colitis. In some embodiments, apremilast is provided for use in methods of treatment, management, and/or prevention any of the above diseases, wherein the method comprises administering apremilast in combination with another drug ("second active agent").

In certain embodiments, the methods encompass synergistic combinations for the treatment, prevention and/or management of psoriasis, ankylosing spondylitis, Behcet's disease, rheumatoid arthritis, atopic dermatitis, Crohn's disease, or ulcerative colitis. Apremilast may also be used to alleviate adverse effects associated with some second active agents.

One or more second active agents can be used in the methods together with apremilast. Second active agents can be administered before, after or simultaneously with apremilast. In some embodiments, the one or more second active agents are selected from the group consisting of anti-inflammatories such as nonsteroidal anti-inflammatory drugs (NSAIDs), immunosuppressants, topical corticosteroids, calcineurin inhibitors, Cox-2 inhibitors, TNF-alpha inhibitors, antirheumatics, antipsoriatics, interleukin inhibitors, narcotic analgesic combinations, salicylates, glucocorticoids and topical rubefacients.

In one embodiment, the second active agent is selected from the group consisting of an anti-inflammatory agent, an immunosuppressant, mycophenolate mofetil, a biologic agent, or a Cox-2 inhibitor.

In one embodiment, the second active agent is sulfasalazine.

In one embodiment, the second active agent is leflunomide.

In one embodiment, the second active agent is an oral corticosteroid.

In one embodiment, the second active agent is etanercept.

In some embodiments, the second active agents may include, but are not limited to, anti-inflammatories such as NSAIDs including, but not limited to, diclofenac (e.g., ARTHROTEC®), diflunisal (e.g., DOLOBID®), etodolac (e.g., LODINE®), fenoprofen (e.g., NALFON®), ibuprofen (e.g., ADVIL, CHILDREN'S ADVIL/MOTRIN, MEDIPREN, MOTRIN, NUPRIN or PEDIACARE FEVER®), indomethacin (e.g., ARTHREXIN®), ketoprofen (e.g., ORUVAIL®), ketorolac (e.g., TORADOL®), fosfomycin tromethamine (e.g., MONURAL®), meclofenamate (e.g., Meclomen®), nabumetone (e.g., RELAFEN®), naproxen (e.g., ANAPROX®, ANAPROX® DS, EC-NAPROSYN®, NAPRELAN® or NAPROSYN®), oxaprozin (e.g., DAYPRO®), piroxicam (e.g., FELDENE®), sulindac (e.g., CLINORIL®), and tolmetin (e.g., TOLECTIN® DS or TOLECTIN®).

In other embodiments, the second active agents may include, but are not limited to, disease-modifying antirheumatic drugs (DMARDs) or immunosuppressants such as, but not limited to, methotrexate (Rheumatrex®), sulfasalazine (Azulfidine®), leflunomide (Arava®), and cyclosporine (Sandimmune® or Neoral®).

In other embodiments, the second active agent is an oral corticosteroid, such as, but not limited to, budesonide (Entocort®), dexamethasone, fludrocortisone (Florinef®, Florinef® acetate), hydrocortisone, methylprednisone, prednisolone, and prednisone.

In other embodiments, the second active agents may include, but are not limited to, mycophenolate mofetil (CellCept®), an immunosuppressive agent widely used in organ transplantation and gaining favor in treating autoimmune and inflammatory skin disorders.

In further embodiments, the second active agents may include, but are not limited to, biologic agents such as etanercept (Enbrel®), infliximab (Remicade®) and adalimumab (Humira®).

In further embodiments, the second active agents may include, but are not limited to, Cox-2 inhibitors such as celecoxib (Celebrex®), valdecoxib (Bextra®) and meloxicam (Mobic®).

In some embodiments, the one or more selective active agents is selected from the group consisting of acitretin, adalimumab, alclometasone, alefacept, aloe vera, amcinonide, ammonium lactate/urea, ammonium lactate/halobetasol, anthralin, benzocaine/pyrilamine/zinc oxide, betamethasone, betamethasone/calcipotriene, calcipotriene, clobetasol, clocortolone, coal tar, coal tar/salicylic acid, corticotropin, cyclosporine, desonide, desoximetasone, diflorasone, fluocinonide, flurandrenolide, halcinonide, halobetasol, hydrocortisone, hydrocortisone/pramoxine, hydroxyurea, infliximab, methotrexate, methoxsalen, mometasone, pramoxine, prednisone, prednisolone, prednicarbate, resorcinol, tazarotene, triamcinolone and ustekinumab.

In some embodiments, the one or more selective active agents is selected from the group consisting of abatacept, acetaminophen, acetaminophen/hydrocodone, acetaminophen/tramadol, adalimumab, alemtuzumab, aluminum hydroxide/aspirin/calcium carbonate/magnesium hydroxide, anakinra, aspirin, auranofin, aurothioglucose, atorvastatin, azathioprine, celecoxib, certolizumab, chondroitin, cortisone, corticotropin, cyclophosphamide, cyclosporine, daclizumab, dexamethasone, diclofenac, diclofenac/misoprostol, diflunisal, doxycycline, esomeprazole, esomeprazole/naproxen, etanercept, etodolac, famotidine, famotidine/ibuprofen, fenoprofen, flurbiprofen, glucosamine, gold sodium thiomalate, golimumab, hydroxychloroquine, ibuprofen, indomethacin, infliximab, interferon, interferon gamma-1b, ketoprofen, lansoprazole, lansoprazole/naproxen, leflunomide, levamisole, meclofenamate, meloxicam, methotrexate, methylprednisone, methylprednisolone, methyl salicylate, minocycline, mycophenolate mofetil, nabumetone, naproxen, oxaprozin, penicillamine, phenytoin, piroxicam, prednisone, primrose oil, rituximab, rofecoxib, salsalate, sulindac, sulfasalazine, tetracycline, tocilizumab, tofacitinib, tolmetin, tramadol, triamcinolone, trolamine salicylate, valdecoxib and pharmaceutically acceptable prodrugs and salts thereof.

In some embodiments, the one or more selective active agents is selected from the group consisting of abatacept, acetaminophen, acetaminophen/hydrocodone, acetaminophen/tramadol, acitretin, adalimumab, alclometasone, alefacept, alemtuzumab, aloe vera, aluminum hydroxide/aspirin/calcium carbonate/magnesium hydroxide, amcinonide, ammonium lactate/urea, ammonium lactate/halobetasol, anakinra, anthralin, aspirin, auranofin, aurothioglucose, atorvastatin, azathioprine, benzocaine/pyrilamine/zinc oxide, betamethasone, betamethasone/calcipotriene, calcipotriene, celecoxib, certolizumab, chondroitin, clobetasol, clocortolone, coal tar, coal tar/salicylic acid, corticotropin, cortisone, cyclophosphamide, cyclosporine, daclizumab, desonide, desoximetasone, dexamethasone, diclofenac, diclofenac/misoprostol, diflorasone, diflunisal, doxycycline, esomeprazole, esomeprazole/naproxen, etanercept, etodolac, famotidine, famotidine/ibuprofen, fenoprofen, fluocinonide, flurandrenolide, flurbiprofen, fostamatinib, glucosamine, gold sodium thiomalate, golimumab, halcinonide, halobetasol, hydrocortisone, hydrocortisone/pramoxine, hydroxyurea, hydroxychloroquine, ibuprofen, indomethacin, infliximab, interferon, interferon gamma-1b, ibrutinib, ketoprofen, lansoprazole, lansoprazole/naproxen, leflunomide, lenalidomide, levamisole, meclofenamate, meloxicam, methotrexate, methoxsalen, methylprednisone, methylprednisolone, methyl salicylate, minocycline, mometasone, mycophenolate mofetil, nabumetone, naproxen, oxaprozin, penicillamine, phenytoin, piroxicam, pomalidomide, pramoxine, prednisone, prednisolone, prednicarbate, primrose oil, resorcinol, rituximab, rofecoxib, salsalate, sulindac, sulfasalazine, tazarotene, tetracycline, tocilizumab, tofacitinib, tolmetin, tramadol, triamcinolone, trolamine salicylate, ustekinumab, valdecoxib, 3-(5-amino-2-methyl-4-oxo-4H-quinazolin-3-yl)-piperidine-2,6-dione, (S)-3-(4-((4-(morpholinomethyl)benzyl)oxy)-1-oxoisoindolin-2-yl)piperidine-2,6-dione and pharmaceutically acceptable prodrugs and salts thereof.

In some embodiments, the one or more selective active agents is selected from the group consisting of a PDE7 inhibitor, a Btk inhibitor, a cereblon targeting agent, a Tyk2 inhibitor, a Syk inhibitor, a JAK inhibitor, a JNK inhibitor, a MK2 inhibitor, an ERP5 inhibitor, a PD-1 inhibitor, a TIMP-3 inhibitor, an IL23p19 inhibitor, an IL-17 blocker, an IKK-2 inhibitor, a LH2B inhibitor, a PKC-theta inhibitor, an IRAK4 inhibitor, a ROCK inhibitor, and a ROR-gamma-T inhibitor.

Administration of apremilast and a second active agent to a patient can occur simultaneously or sequentially by the same or different routes of administration. The suitability of a particular route of administration employed for a particular second active agent will depend on the second active agent itself (e.g., whether it can be administered orally or topically without decomposing) and the subject being treated. Particular routes of administration for the second active agents or ingredients are known to those of ordinary skill in the art. See, e.g., *The Merck Manual*, 448 (17$^{th}$ ed., 1999).

The amount of second active agent administered can be determined based on the specific agent used, the subject being treated, the severity and stage of disease and the amount(s) of apremilast and any optional additional second active agents concurrently administered to the patient. Those of ordinary skill in the art can determine the specific amounts according to conventional procedures known in the art. In the beginning, one can start from the amount of the second active agent that is conventionally used in the therapies and adjust the amount according to the factors described above. See, e.g., *Physician's Desk Reference* (59$^{th}$ Ed., 2005).

In certain embodiments, the second active agent is administered orally, topically, transdermally, intravenously or subcutaneously. In certain embodiments, the second active agent is administered once to four times daily. In certain embodiments, the second active agent is administered once to four times monthly. In certain embodiments, the second active agent is administered once every week. In certain embodiments, the second active agent is administered once every other week. In certain embodiments, the second active agent is administered once every month. In certain embodiments, the second active agent is administered once every two months. In certain embodiments, the second active agent is administered once every three months. In certain embodiments, the second active agent is administered in an amount of from about 1 to about 1,000 mg, from about 5 to about 500 mg, from about 10 to about 350 mg or from about 50 to about 200 mg. The specific amount of the second active agent will depend on the specific agent used, the age of the subject being treated, the severity and stage of disease and the amount(s) of apremilast and any optional additional second active agents concurrently administered to the patient.

4.3 Apremilast

Apremilast is an inhibitor of phosphodiesterase 4 (PDE4) specific for cyclic adenosine monophosphate (cAMP).

PDE4 inhibition results in increased intracellular cAMP levels and is effective in the inhibition of inflammatory mediator release.

Without being limited by theory, apremilast is believed to be (+) enantiomer of 2-[1-(3-ethoxy-4-methoxyphenyl)-2-methanesulfonylethyl]-4-acetylaminoisoindolin-1,3-dione having the following structure:

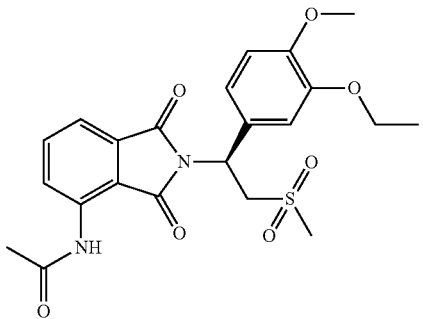 [SMILES: CCOc1cc([C@@H](CS(C)(=O)=O)N2C(=O)c3cccc(NC(C)=O)c3C2=O)ccc1OC]

Apremilast may be prepared according to methods disclosed in U.S. Pat. Nos. 6,962,940; 7,208,516; 7,427,638; or 7,893,101, the entirety of each which is incorporated herein by reference. In a specific method, apremilast may be prepared, for example, by the following process.

A stirred solution of 1-(3-ethoxy-4-methoxyphenyl)-2-methylsulfonylethylamine (1.0 g, 3.7 mmol) and 3-acetamidophthalic anhydride (751 mg, 3.66 mmol) in acetic acid (20 mL) was heated at reflux for 15 h. The solvent was removed in vacuo to yield an oil. Chromatography of the resulting oil yielded the product as a yellow solid (1.0 g, 59% yield): mp, 144° C.; $^1$H NMR (CDCl$_3$) δ: 1.47 (t, J=7.0 Hz, 3H, CH$_3$), 2.26 (s, 3H, CH$_3$), 2.88 (s, 3H, CH$_3$), 3.75 (dd, J=4.4, 14.3 Hz, 1H, CH), 3.85 (s, 3H, CH3), 4.11 (q, J=7 Hz, 2H, CH$_2$), 5.87 (dd, J=4.3, 10.5 Hz, 1H, NCH), 6.82-6.86 (m, 1H, Ar), 7.09-7.11 (m, 2H, Ar), 7.47 (d, J=7 Hz, 1H, Ar), 7.64 (t, J=8 Hz, 1H, Ar), 8.74 (d, J=8 Hz, 1H, Ar), 9.49 (br s, 1H, NH); $^{13}$C NMR (CDCl$_3$) δ: 14.61, 24.85, 41.54, 48.44, 54.34, 55.85, 64.43, 111.37, 112.34, 115.04, 118.11, 120.21, 124.85, 129.17, 130.96, 136.01, 137.52, 148.54, 149.65, 167.38, 169.09, 169.40; Anal Calc'd. for C$_{22}$H$_{24}$NO$_7$S: C, 57.38; H, 5.25; N, 6.08. Found: C, 57.31; H, 5.34; N, 5.83.

Preparation of 3-aminophthalic acid: 10% Pd/C (2.5 g), 3-nitrophthalic acid (75.0 g, 355 mmol) and ethanol (1.5 L) were charged to a 2.5 L Parr hydrogenator under a nitrogen atmosphere. Hydrogen was charged to the reaction vessel for up to 55 psi. The mixture was shaken for 13 hours, maintaining hydrogen pressure between 50 and 55 psi. Hydrogen was released and the mixture was purged with nitrogen 3 times. The suspension was filtered through a celite bed and rinsed with methanol. The filtrate was concentrated in vacuo. The resulting solid was reslurried in ether and isolated by vacuum filtration. The solid was dried in vacuo to a constant weight, affording 54 g (84% yield) of 3-aminopthalic acid as a yellow product. $^1$H-NMR (DMSO-d6) δ: 3.17 (s, 2H), 6.67 (d, 1H), 6.82 (d, 1H), 7.17 (t, 1H), 8-10 (br, s, 2H); $^{13}$C-NMR (DMSO-d6) δ: 112.00, 115.32, 118.20, 131.28, 135.86, 148.82, 169.15, 170.09.

Preparation of 3-aminophthalic anhydride: A 1 L 3-necked round bottom flask was equipped with a mechanical stirrer, thermometer, and condenser and charged with 3-aminophthalic acid (108 g, 596 mmol) and acetic anhydride (550 mL). The reaction mixture was heated to reflux for 3 hours and cooled to about 25° C. and further to 0-5° C. for another 1 hour. The crystalline solid was collected by vacuum filtration and washed with ether. The solid product was dried in vacuo at ambient temperature to a constant weight, giving 75 g (61% yield) of 3-acetamidopthalic anhydride as a white product. $^1$H-NMR (CDCl$_3$) δ: 2.21 (s, 3H), 7.76 (d, 1H), 7.94 (t, 1H), 8.42 (d, 1H), 9.84 (s, 1H).

Resolution of 2-(3-ethoxy-4-methoxyphenyl-1-(methylsulphonyl)-eth-2-ylamine: A 3 L 3-necked round bottom flask was equipped with a mechanical stirrer, thermometer, and condenser and charged with 2-(3-ethoxy-4-methoxyphenyl)-1-(methylsulphonyl)-eth-2-ylamine (137.0 g, 500 mmol), N-acetyl-L-leucine (52 g, 300 mmol), and methanol (1.0 L). The stirred slurry was heated to reflux for 1 hour. The stirred mixture was allowed to cool to ambient temperature and stirring was continued for another 3 hours at ambient temperature. The slurry was filtered and washed with methanol (250 L). The solid was air-dried and then dried in vacuo at ambient temperature to a constant weight, giving 109.5 g (98% yield) of the crude product (85.8% ee). The crude solid (55.0 g) and methanol (440 mL) were brought to reflux for 1 hour, cooled to room temperature and stirred for an additional 3 hours at ambient temperature. The slurry was filtered and the filter cake was washed with methanol (200 mL). The solid was air-dried and then dried in vacuo at 30° C. to a constant weight, yielding 49.6 g (90% recovery) of (S)-2-(3-ethoxy-4-methoxyphenyl)-1-(methylsulphonyl)-eth-2-ylamine-N-acetyl-L-leucine salt (98.4% ee). Chiral HPLC (1/99 EtOH/20 mM KH$_2$PO$_4$ @ pH 7.0, Ultron Chiral ES-OVS from Agilent Technologies, 150 mm×4.6 mm, 0.5 mL/min., @ 240 nm): 18.4 min (S-isomer, 99.2%), 25.5 min (R-isomer, 0.8%).

Final preparation of apremilast: A 500 mL 3-necked round bottom flask was equipped with a mechanical stirrer, thermometer, and condenser. The reaction vessel was charged with (S)-2-(3-ethoxy-4-methoxyphenyl)-1-(methylsulphonyl)-eth-2-yl amine N-acetyl-L-leucine salt (25 g, 56 mmol, 98% ee), 3-acetamidophthalic anhydride (12.1 g, 58.8 mmol), and glacial acetic acid (250 mL). The mixture was refluxed over night and then cooled to <50° C. The solvent was removed in vacuo, and the residue was dissolved in ethyl acetate. The resulting solution was washed with water (250 mL×2), saturated aqueous NaHCO$_3$ (250 mL×2), brine (250 mL×2), and dried over sodium sulphate. The solvent was evaporated in vacuo, and the residue recrystallized from a binary solvent containing ethanol (150 mL) and acetone (75 mL). The solid was isolated by vacuum filtration and washed with ethanol (100 mL×2). The product was dried in vacuo at 60° C. to a constant weight, affording 19.4 g (75% yield) of apremilast with 98% ee. Chiral HPLC (15/85 EtOH/20 mM KH$_2$PO$_4$ @ pH 5, Ultron Chiral ES-OVS from Agilent Technology, 150 mm×4.6 mm, 0.4 mL/min, @ 240 nm): 25.4 min (S-isomer, 98.7%), 29.5 min (R-isomer, 1.2%). $^1$H-NMR (CDCl$_3$) δ: 1.47 (t, 3H), 2.26 (s, 3H), 2.87 (s, 3H), 3.68-3.75 (dd, 1H), 3.85 (s, 3H), 4.07-4.15 (q, 2H), 4.51-4.61 (dd, 1H), 5.84-5.90 (dd, 1H), 6.82-8.77 (m, 6H), 9.46 (s, 1H); $^{13}$C-NMR (DMSO-d6) δ: 14.66, 24.92, 41.61, 48.53, 54.46, 55.91, 64.51, 111.44, 112.40, 115.10, 118.20, 120.28, 124.94, 129.22, 131.02, 136.09, 137.60, 148.62, 149.74, 167.46, 169.14, 169.48.

Pharmaceutical Compositions and Dosage Forms

Pharmaceutical compositions can be used in the preparation of individual, single unit dosage forms. Pharmaceutical compositions and dosage forms can comprise apremilast or a pharmaceutically acceptable salt or solvate thereof and a second active agent. Examples of the optional second active agents are disclosed herein (see, e.g., section 4.2.1). Pharmaceutical compositions and dosage forms can further comprise one or more carriers, excipients or diluents.

The pharmaceutical compositions provided herein are suitable for oral administration can be presented as discrete dosage forms, such as, but not limited to, tablets (e.g., chewable tablets), caplets, capsules and liquids (e.g., flavored syrups). Such dosage forms contain predetermined amounts of active ingredients and can be prepared by methods of pharmacy well known to those skilled in the art. See generally, *Remington's Pharmaceutical Sciences,* 20th ed., Mack Publishing, Easton Pa. (2,000).

Typical oral dosage forms are prepared by combining the active ingredients in an intimate admixture with at least one excipient according to conventional pharmaceutical compounding techniques. Excipients can take a wide variety of forms depending on the form of preparation desired for administration. Non-limiting examples of excipients suitable for use in oral liquid or aerosol dosage forms include water, glycols, oils, alcohols, flavoring agents, preservatives and coloring agents. Non-limiting examples of excipients suitable for use in solid oral dosage forms (e.g., powders, tablets, capsules and caplets) include starches, sugars, microcrystalline cellulose, diluents, granulating agents, lubricants, binders and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers or both and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Non-limiting examples of excipients that can be used in oral dosage forms include binders, fillers, disintegrants and lubricants. Non-limiting examples of binders suitable for use in pharmaceutical compositions and dosage forms include corn starch, potato starch or other starches, gelatin, natural and synthetic gums such as *acacia,* sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose and mixtures thereof.

Non-limiting examples of suitable forms of microcrystalline cellulose include, but are not limited to, the materials sold as AVICEL® (microcrystalline cellulose) PH-101, AVICEL® (microcrystalline cellulose) PH-103, AVICEL RC-5810 (crystalline cellulose and carboxymethylcellulose sodium), AVICEL® (microcrystalline cellulose) PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581® (crystalline cellulose and carboxymethylcellulose sodium). Suitable anhydrous or low moisture excipients or additives include AVICEL-PH-103® (microcrystalline cellulose) PH-103 and Starch 1500® LM (pre gelatinized starch).

Non-limiting examples of fillers suitable for use in the pharmaceutical compositions and dosage forms disclosed herein include talc, calcium carbonate (e.g., granules or powder), microcrystalline cellulose, powdered cellulose, dextrates, kaolin, mannitol, silicic acid, sorbitol, starch, pre-gelatinized starch and mixtures thereof. The binder or filler in pharmaceutical compositions is typically present in from about 50 to about 99 weight percent of the pharmaceutical composition or dosage form.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation and is readily discernible to those of ordinary skill in the art. Typical pharmaceutical compositions comprise from about 0.5 to about 15 weight percent of disintegrant, preferably from about 1 to about 5 weight percent of disintegrant.

Non-limiting examples of disintegrants that can be used in pharmaceutical compositions and dosage forms include agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums and mixtures thereof.

Non-limiting examples of lubricants that can be used in pharmaceutical compositions and dosage forms include calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laureate, agar and mixtures thereof. Additional lubricants include, for example, a syloid silica gel (AEROSIL200® (silica), manufactured by W.R. Grace Co. of Baltimore, Md.), a coagulated aerosol of synthetic silica (marketed by Degussa Co. of Plano, Tex.), CAB-O-SIL® (fumed silica) (a pyrogenic silicon dioxide product sold by Cabot Co. of Boston, Mass.) and mixtures thereof. If used at all, lubricants are typically used in an amount of less than about 1 weight percent of the pharmaceutical compositions or dosage forms into which they are incorporated.

Non-limiting examples of dosage forms include tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions or a water-in-oil liquid emulsions), solutions and elixirs.

The composition, shape and type of dosage forms will typically vary depending on their use. For example, a dosage form used in the acute treatment of a disease may contain larger amounts of one or more of the active ingredients it comprises than a dosage form used in the chronic treatment of the same disease. These and other ways in which specific dosage forms will vary from one another will be readily apparent to those skilled in the art. See, e.g., *Remington's Pharmaceutical Sciences,* 20th ed., Mack Publishing, Easton Pa. (2,000).

Typical pharmaceutical compositions and dosage forms comprise one or more excipients. Suitable excipients are well known to those skilled in the art of pharmacy and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. The suitability of a particular excipient may also depend on the specific active ingredients in the dosage form. For example, the decomposition of some active ingredients can be accelerated by some excipients such as lactose or when exposed to water. Active ingredients that comprise primary or secondary amines are particularly susceptible to such accelerated decomposition.

In certain embodiments, provided herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Non-limiting examples of suitable packaging include hermetically sealed foils, plastics, unit dose containers (e.g., vials), blister packs and strip packs.

Also provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers or salt buffers. Like the amounts and types of excipients, the amounts and specific types of active ingredients in a dosage form may differ depending on factors such as, but not limited to, the route by which it is to be administered to patients. However, typical oral dosage forms comprise apremilast in an amount of 10 mg, 20 mg or 30 mg. In a particular embodiments, the oral dosage forms are 10 mg, 20 mg or 30 mg tablets. Each tablet contains apremilast as the active ingredient and the following inactive ingredients: lactose monohydrate, microcrystalline cellulose, croscarmellose sodium, magnesium stearate, polyvinyl alcohol, titanium dioxide, polyethylene glycol, talc, iron oxide red, iron oxide yellow (20 and 30 mg only), and iron oxide black (30 mg only).

Delayed Release Dosage Forms

In certain embodiments, active ingredients can be administered by controlled release means or by delivery devices that are well known to those of ordinary skill in the art. Non-limiting examples of controlled release means or delivery devices include those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556 and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres or a combination thereof to provide the desired release profile in varying proportions. Suitable controlled-release formulations known to those of ordinary skill in the art, including those described herein, can be readily selected for use with the active ingredients. In certain embodiments, provided herein are single unit dosage forms suitable for oral administration such as, but not limited to, tablets, capsules, gelcaps and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency and increased patient compliance. In addition, controlled-release formulations can be used to affect the time of onset of action or other characteristics, such as blood levels of the drug and can thus affect the occurrence of side (e.g., adverse) effects.

Most controlled-release formulations are designed to initially release an amount of drug (active ingredient) that promptly produces the desired therapeutic effect and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water or other physiological conditions or compounds.

5. EXAMPLES

Some embodiments are illustrated by the following non-limiting examples. The examples should not be construed as a limitation in the scope thereof.

The recommended dose of apremilast is 30 mg twice daily taken orally for treating patients with psoriasis, ankylosing spondylitis, Behcet's disease, rheumatoid arthritis, atopic dermatitis, Crohn's disease or ulcerative colitis. The recommended dosage titration schedule is described below.

(i) 10 mg in the morning on the first day of administration;

(ii) 10 mg in the morning and 10 mg after noon on the second day of administration;

(iii) 10 mg in the morning and 20 mg after noon on the third day of administration;

(iv) 20 mg in the morning and 20 mg after noon on the fourth day of administration;

(v) 20 mg in the morning and 30 mg after noon on the fifth day of administration; and (vi) 30 mg in the morning and 30 mg after noon on the sixth and every subsequent day of administration.

Other titration schedules with a target dose of 20 mg BID and 40 mg BID are also described herein. The dosage titration schedule can be used for patients with psoriasis, ankylosing spondylitis, Behcet's disease, rheumatoid arthritis, atopic dermatitis, or ulcerative colitis.

This dosage titration is intended to reduce the gastrointestinal symptoms that may be associated with initial treatment. Apremilast can be administered without regard to meals.

5.1. Clinical Activity of Apremilast in Patients with Psoriasis in a Clinical Study (Esteem 1)

A randomized, double-blind, placebo controlled, multicenter clinical study was performed in patients with moderate to severe plaque psoriasis who had a body surface area (BSA) involvement of ≥10%, static Physician Global Assessment (sPGA) of ≥3 (moderate or severe disease), Psoriasis Area and Severity Index (PASI) score≥12, and who were candidates for phototherapy or systemic therapy. In the study 844 patients were enrolled; patients ranged in age from 18 to 83 years, with an overall median age of 46 years. The mean baseline body surface area (BSA) involvement was 25.19% (median 21.0%), the mean baseline PASI score was 19.07 (median 16.80), and the proportion of patients with sPGA score of 3 (moderate) and 4 (severe) at Baseline were 70.0% and 29.8%, respectively. Patients were randomized to Apremilast, in an amount of 30 mg twice per day (after the initial dose titration schedule) or placebo for the first 16 weeks, and from Weeks 16 to 32, all patients received Apremilast in an amount of 30 mg twice per day.

Dose Titration Schedule:
Target Dose: 30 mg (po) BID
Day 1: 10 mg in the morning
Day 2: 10 mg morning; 10 mg after noon
Day 3: 10 mg morning; 20 mg after noon
Day 4: 20 mg morning; 20 mg after noon
Day 5: 20 mg morning; 30 mg after noon
Day 6 onward: 30 mg BID During the Randomized Treatment Withdrawal Phase (Weeks 32-52), patients originally randomized to Apremilast who achieved at least a 75% reduction in PASI score (PASI-75) at Week 32 were re-randomized to either placebo or Apremilast 30 mg BID. Patients who were re-randomized to placebo and who lost PASI-75 response at Week 32 compared to Baseline, were retreated with Apremilast 30 mg BID. Patients who did not achieve the designated PASI response by Week 32, or who were initially randomized to placebo, remained on Apremilast until Week 52.

Results:

The primary endpoint, PASI 75 at Week 16, was achieved by a significantly greater proportion of patients randomized to apremilast (186 [33.1%]) than placebo (15 [5.3%]; 95% CI 23.1-32.5; p<0.0001; Table 1). An sPGA score of 0 or 1 at Week 16, the major secondary endpoint, was achieved by a significantly greater proportion of patients randomized to apremilast than placebo (122 [21.7%] versus 11 [3.9%]; 95% CI 13.7-21.9; p<0.0001). Similar results were obtained in sensitivity analyses including nonresponder imputation for PASI 75 (p<0.0001) and sPGA (p<0.0001) responses. Non-overlapping confidence intervals (representing a clinically meaningful difference) between apremilast and placebo in the mean percentage improvement in PASI from baseline were detected as early as Week 2. Other endpoints at Week 16, including PASI-50 and PASI-90 response, mean percentage change in PASI score, NAPSI score, mean change from baseline in DLQI score, and DLQI response (decrease of at least five points in DLQI total score), were all significantly greater with apremilast than placebo (all p<0.0001). For patients with nail and scalp psoriasis at baseline, at least a 50% improvement in baseline NAPSI (NAPSI 50) response and ScPGA response (score of 0 [clear] or 1 [minimal]) were achieved by a significantly greater proportion of patients randomized to apremilast than placebo at Week 16 (both NAPSI-50 and ScPGA p<0.0001).

Responses to apremilast were generally maintained from Weeks 16 to 32. At Week 32, patients initially randomized to placebo at baseline who were switched to apremilast at Week 16 had similar response rates as those receiving apremilast from baseline. PASI 50 responses and DLQI scores at Week 32 showed similar time-response profiles.

In the randomized treatment withdrawal phase, 154 patients randomized to apremilast at baseline who achieved PASI 75 responses at Week 32 were re-randomized to continue apremilast (n=77) or switch to placebo (n=77). Of the 77 patients re-randomized to apremilast at Week 32, 47 (61.0%) had PASI-75 response at Week 52, and 58 (75.3%) had at least 70% improvement in PASI score from baseline. Mean PASI responses were generally maintained through Week 52 in patients re-randomized to apremilast. Mean percentage change from baseline in PASI score at Week 52 was 80.5%. Among patients re-randomized to placebo, 13 (16.9%) did not resume apremilast before Week 52. At Week 52, mean percentage change in PASI score from baseline in these 13 patients was 88.1%; nine (11.7%) patients re-randomized to placebo achieved PASI 75 response at Week 52. 64 patients re-initiated apremilast before Week 52 after losing PASI 75 responses; of these, 45 (70.3%) regained PASI 75 response after re-treatment (re-treatment time ranged from 3.4 to 22.1 weeks). Median time to first loss of PASI 75 after re-randomization was 5.1 weeks for patients re-randomized to placebo and 17.7 weeks for patients re-randomized to apremilast.

The 5 most common adverse events (AEs) were diarrhea, nausea, upper respiratory tract infection, tension headache, and headache. Discontinuations due to AEs were nausea (1.2%), diarrhea (0.8%), headache (0.4%), and tension headache (0.2%). No patient discontinued due to upper respiratory tract infection.

Conclusion

The study results showed that Apremilast significantly improved signs and symptoms of psoriasis. The majority of adverse events was mild to moderate and did not lead to discontinuation. The results were very promising with respect to efficacy and safety of Apremilast in psoriasis patients.

TABLE 1

Clinical response across efficacy endpoints

| | Placebo-controlled phase (Week 16) | |
|---|---|---|
| | Placebo n = 282 | Apremilast 30 mg twice daily n = 562 |
| Primary endpoint | | |
| PASI-75 | 15 (5.3%) | 186 (33.1%)* |
| Major secondary endpoint | | |
| sPGA respons[§] | 11 (3.9%) | 122 (21.7%)* |
| Other endpoints | | |
| PASI-50 | 48 (17.0%) | 330 (58.7%)* |
| PASI-90 | 1 (0.4%) | 55 (9.8%)* |
| Percentage change in PASI score, mean (SD) | −16.7 (31.52) | −52.1 (32.81)* |
| Percentage change in PASI score, median (range) | −14.0 (−91 to 72) | −59.0 (−100 to 86) |
| Mean Change in DLQI score | −2.1 (5.69) | −6.6 (6.66)* |
| Patients with baseline DLQI >5 | n = 236 | n = 459 |
| DLQI response[‡] | 79 (33.5%) | 322 (70.2%)* |
| DLQI + PASI-50 response[∥] | 26 (11.0%) | 221 (48.1%)* |
| Patients with nail psoriasis at baseline | n = 195 | n = 363 |
| Percentage change in NAPSI score[¶] | 6.5 (60.57) | −22.5 (54.86)* |
| NAPSI-50[¶] | 29 (14.9%) | 121 (33.3%)* |
| Patients with scalp psoriasis at baseline | n = 189 | n = 374 |
| ScPGA score 0-1[#] | 33 (17.5%) | 174 (46.5%)* |

Data are n (%), mean (SD), or median (range).
PASI-75 = 75% reduction from baseline psoriasis area and severity index score;
sPGA = static physician global assessment;
PASI-50 = 50% reduction from baseline psoriasis area and severity index score;
PASI-90 = 90% reduction from baseline psoriasis area and severity index score;
DLQI = dermatology life quality index; NAPSI = nail psoriasis severity index;
NAPSI-50 = at least a 50% improvement from baseline nail psoriasis severity index score;
ScPGA = scalp physician global assessment.
Week 16 missing data were handled with last-observation-carried-forward methodology.
*P < 0.0001 versus placebo.
[§]sPGA score of clear (0) or almost clear (1) with at least a two-point reduction from baseline.
[‡]Decrease of at least five points in DLQI total score in patients with baseline total DLQI scor greater than 5. A reduction in score indicated improvement.
[∥]Decrease of at least five points in DLQI total score and PASI-50 achievement in patients with baseline total DLQI score greater than 5.
[¶]Patients with nail psoriasis (score of at least 1) at baseline. A reduction in the NAPSI score indicated improvement.
[#]Patients with ScPGA score of at least 3 at baseline.

5.2. Clinical Activity of Apremilast in Patients with Psoriasis in a Clinical Study (Esteem 2)

A randomized, double-blind, placebo controlled, multi-center clinical study was performed in patients with moderate to severe plaque psoriasis who had a body surface area (BSA) involvement of ≥10%, static Physician Global Assessment (sPGA) of ≥3 (moderate or severe disease), Psoriasis Area and Severity Index (PASI) score≥12, and who were candidates for phototherapy or systemic therapy. In the study 413 patients were enrolled; patients ranged in age from 18 to 83 years, with an overall median age of 46 years. The mean baseline body surface area (BSA) involvement was 25.19% (median 21.0%), the mean baseline PASI score was 19.07 (median 16.80), and the proportion of patients with sPGA score of 3 (moderate) and 4 (severe) at Baseline were 70.0% and 29.8%, respectively. Patients were randomized to Apremilast in an amount of 30 mg twice per day (after the initial dose titration schedule) or placebo for the first 16 weeks, and from Weeks 16 to 32, all patients received Apremilast in an amount of 30 mg twice per day.

Dose Titration Schedule:
Target Dose: 30 mg (po) BID
Day 1: 10 mg in the morning
Day 2: 10 mg morning; 10 mg after noon
Day 3: 10 mg morning; 20 mg after noon
Day 4: 20 mg morning; 20 mg after noon
Day 5: 20 mg morning; 30 mg after noon
Day 6 onward: 30 mg BID During the Randomized Treatment Withdrawal Phase (Weeks 32-52), patients originally randomized to Apremilast who achieved at least a 50% reduction in PASI score (PASI-50) were re-randomized to either placebo or Apremilast 30 mg BID. Patients who were re-randomized to placebo and who lost 50% of the improvement in PASI at Week 32 compared to Baseline, were retreated with Apremilast 30 mg BID. Patients who did not achieve the designated PASI response by Week 32, or who were initially randomized to placebo, remained on Apremilast until Week 52.

Results:

Placebo-controlled phase (Weeks 0 to 16). At Week 16, significantly more patients receiving apremilast achieved a PASI-75 response (primary endpoint) vs. placebo (28.8% vs. 5.8%; P<0.0001; Table 2). The major secondary endpoint, sPGA score of 0 or 1 at Week 16, was also achieved by significantly more patients receiving apremilast vs. placebo (20.4% vs. 4.4%; P<0.0001). Significantly more patients receiving apremilast achieved PASI-50 and PASI-90 responses vs. placebo (55.5% vs. 19.7%; P<0.0001 and 8.8% vs. 1.5%; P=0.0042) at Week 16. Results of the NRI sensitivity analysis were similar to the primary analysis (Table 2). The mean/median percent change from baseline in PASI score was −50.9%/−56.0% for apremilast vs. −15.8%/−18.0% for placebo (P<0.0001, mean change) at Week 16. Non-overlapping confidence intervals (representing a clinically meaningful difference) between apremilast and placebo in the mean percentage improvement in PASI from baseline were detected as early as Week 2, the first post-baseline visit.

Significant improvements at Week 16 were seen with Apremilast vs. placebo based on other efficacy endpoints, including PASI response and Dermatology Life Quality Index (DLQI) score and response (all P<0.0001; Table 2). At Week 16, among patients with nail psoriasis (Nail Psoriasis Severity Index [NAPSI]≥1), NAPSI-50 response was achieved by significantly more patients receiving apremilast vs. placebo (44.6% vs. 18.7%; P<0.0001; Table 2). Similarly, among patients with scalp psoriasis (Scalp Physician Global Assessment [ScPGA]≥3) at baseline, ScPGA score of 0 (clear) or 1 (minimal) was achieved by significantly more patients receiving apremilast vs. placebo (40.9% vs. 17.2%; P<0.0001; Table 2) and among patients with palmoplantar psoriasis at baseline (Palmoplantar Psoriasis Physician Global Assessment [PPPGA]≥3), a score of 0 (clear) or 1 (almost clear) was achieved by significantly more patients receiving apremilast vs. placebo (65.4% vs. 31.3%; P=0.0315; Table 2).

At Week 16, mean improvements from baseline in pruritus visual analog scale (VAS; mm) scores were significantly greater with apremilast vs. placebo (−33.5 vs. −12.2; P<0.0001). Mean changes from baseline with apremilast represented a decrease of nearly 50% in pruritus severity. At Week 16, mean improvements in skin discomfort/pain VAS (mm) scores were also significantly greater with apremilast vs. placebo (−28.5 vs. −9.5; P<0.0001; Table 2), which also represented a decrease of nearly 50% in severity from baseline. Non-overlapping confidence intervals (representing a clinically meaningful difference) between apremilast and placebo in improvement in pruritus and skin discomfort/pain from baseline were detected as early as Week 2.

Maintenance Phase (Weeks 16 to 32).

PASI-50, PASI-75, and PASI-90 responses were generally maintained from Weeks 16 to 32 in patients treated with apremilast from baseline. PASI, sPGA, and DLQI responses were also generally maintained from Weeks 16 to 32 in patients treated with apremilast from baseline and placebo patients who switched to apremilast at Week 16 had response rates similar to those in patients receiving apremilast in both treatment periods.

Randomized Treatment Withdrawal Phase (Weeks 32 to 52).

For the randomized treatment withdrawal phase, among the 123 patients initially randomized to apremilast who achieved≥PASI-50 at Week 32, 61 and 62 patients were re-randomized to apremilast and placebo, respectively. Of patients re-randomized to apremilast, 80.3% had a PASI-50 response and 60.7% had ≥70% improvement from baseline in PASI score at Week 52; mean percent change in PASI at Week 52 was −74.4%. Among the 36 patients re-randomized to apremilast who were also PASI-75 responders at Week 32, 66.7% had PASI-75 at Week 52. Among patients initially randomized to placebo at baseline who switched to apremilast at Week 16 and achieved PASI-50 at Week 32, 83.1% had PASI-50 at Week 52; mean percent change in PASI from baseline was −71.8%.

Of the 62 patients re-randomized to placebo at Week 32, 30 did not resume treatment with apremilast before Week 52 (these patients did not lose 50% of their PASI improvement prior to Week 52). Among patients re-randomized to placebo, 24.2% had a PASI-50 response at Week 52. Thirty-two (32) patients re-randomized to placebo lost 50% of their PASI improvement and re-initiated treatment with apremilast before Week 52; 65.6% of these patients regained PASI-50 response after re-treatment (re-treatment time ranged from 2.6 to 18.3 weeks). The median time to first loss of 50% of the PASI improvement obtained at Week 32 was 12.4 weeks among patients re-randomized to placebo and 21.9 weeks among patients re-randomized to apremilast (P<0.0001).

Most patients initially randomized to apremilast who did not achieve PASI-50 at Week 32 continued to experience mean PASI improvements through Week 52. At Week 52, PASI-50 was achieved by 32.8% of these patients; mean percent change from baseline in PASI score was −45.7%. Among patients randomized to placebo at baseline who switched to apremilast at Week 16 and who did not achieve PASI-50 at Week 32, 16.0% achieved PASI-50 at Week 52; mean percent change from baseline was −24.7%.

The 5 most common adverse events (AEs) were diarrhea, nausea, upper respiratory tract infection, tension headache, and headache. Discontinuations due to AEs were nausea (1.2%), diarrhea (0.8%), headache (0.4%), and tension headache (0.2%). No patient discontinued due to upper respiratory tract infection.

Conclusion

The study results showed that Apremilast significantly improved signs and symptoms of psoriasis. The majority of adverse events was mild to moderate and did not lead to discontinuation. The results were very promising and consistent with efficacy and safety of Apremilast in psoriasis patients.

TABLE 2

Clinical response across efficacy endpoints at Week 16 (placebo-controlled phase)

| | Placebo n = 137 | Apremilast 30 mg BID n = 274 |
|---|---|---|
| Primary endpoint | | |
| PASI-75, % (LOCF) | 5.8 | 28.8* |
| PASI-75, % (NRI) | 5.1 | 28.1* |
| Major secondary endpoint | | |
| sPGA score 0 (clear) or 1 (almost clear)$^§$, % (LOCF) | 4.4 | 20.4* |
| sPGA score 0 (clear) or 1 (almost clear), % (NRI) | 3.6 | 19.7* |
| Other endpoints | | |
| PASI-50, % (LOCF) | 19.7 | 55.5* |
| PASI-50, % (NRI) | 17.5 | 53.6* |
| PASI-90, % (LOCF) | 1.5 | 8.8$^‡$ |
| Mean % change in PASI score | −15.8 | −50.9* |
| Median % change in PASI score | −18.0 | −56.0 |
| Mean change in DLQI score | −2.8 | −6.7* |
| Mean change in pruritus VAS score, mm | −12.2 | −33.5* |
| Mean change in skin discomfort/pain VAS score, mm | −9.5 | −28.5* |
| Patients with baseline DLQI >5 | n = 119 | n = 226 |
| DLQI response (decrease of ≥5 points)$^|$, % | 42.9 | 70.8* |
| DLQI (decrease of ≥5 points) + PASI-50 response$^#$, % | 13.4 | 49.1* |
| Patients with nail psoriasis | n = 91 | n = 175 |
| Mean % change in NAPSI score$^¶$ | −7.1 | −29.0** |
| NAPSI-50$^¶$, % | 18.7 | 44.6* |
| Patients with scalp psoriasis | n = 93 | n = 176 |
| ScPGA score 0 (clear) or 1 (minimal)$^{§§}$, % | 17.2 | 40.9* |
| Patients with palmoplantar psoriasis | n = 16 | n = 26 |
| PPPGA score 0 (clear) or 1 (almost clear)$^{‡‡}$, % | 31.3 | 65.4$^{||}$ |

Note:
Week 16 missing data were handled with last-observation-carried-forward methodology, except where noted for non-responder imputation. Decreases in DLQI score, pruritus VAS score, skin discomfort/pain VAS score, and NAPSI score indicate improvement.
*P < 0.0001 vs. placebo.
$^§$sPGA score of 0 (clear) or 1 (almost clear) with a ≥2-point reduction from baseline.
$^‡$P = 0.0042 vs. placebo.
$^|$Decrease of ≥5 points in DLQI total score in patients with a baseline total DLQI score >5.
$^#$Decrease of ≥5 points in DLQI total score and PASI-50 achievement in patients with baseline total DLQI score >5.
$^¶$Patients with nail psoriasis (score ≥1) at baseline.
**P = 0.0052 vs. placebo.
$^{§§}$Patients with ScPGA score of ≥3 (moderate to very severe) at baseline.
$^{‡‡}$Patients with PPPGA score ≥3 (moderate to severe) at baseline.
$^{||}$P = 0.0315 vs. placebo.
DLQI, Dermatology Life Quality Index;
LOCF, last observation carried forward;
NAPSI, Nail Psoriasis Severity Index;
NRI, non-responder imputation;
PASI, Psoriasis Area and Severity Index;
PPPGA, Palmoplantar Psoriasis Physician Global Assessment;
scPGA, Scalp Physician Global Assessment;
sPGA, static Physician Global Assessment;
VAS = visual analog scale.

5.3. Clinical Activity of Apremilast in Patients with Atopic Dermatitis in a Clinical Study An open-label pilot study examining 2 doses of apremilast was performed in patients with adult atopic dermatitis. A total of 16 patients with moderate to severe atopic dermatitis were treated with apremilast in 2 different cohorts. Cohort 1 consisted of 6 adult patients treated with apremilast according to the dosing schedule below, 20 mg twice a day, for a total of 3 months. At the conclusion of this cohort, the US Food and Drug Administration (FDA) approved a higher dose and longer treatment course for apremilast. Thus, a second cohort was initiated. Cohort 2 consisted of 10 adult patients treated with apremilast according to the dosing schedule below, 30 mg twice a day, for a total of 6 months. A diagnosis of atopic dermatitis was determined by the Hanifin-Rajka criteria.

Dose Titration Schedule:
Target Dose: 20 mg (po) BID
Day 1: 10 mg in the morning
Day 2: 10 mg BID
Day 3: 10 mg morning; 20 mg after noon
Day 4 onward: 20 mg BID
Dose Titration Schedule:
Target Dose: 30 mg (po) BID
Day 1: 10 mg in the morning
Day 2: 10 mg BID
Day 3: 10 mg morning; 20 mg after noon
Day 4: 20 mg BID
Day 5: 20 mg morning; 30 mg after noon
Day 6 onward: 30 mg BID In certain patients, a dosing schedule with an amount up to 40 mg BID is used.

Efficacy of apremilast was assessed at each study visit using the Eczema Area and Severity Index (EASI), Dermatology Life Quality Index (DLQI), investigator global assessment (IGA), and the visual analog scale (VAS) for pruritus. Patients were monitored for adverse events (AEs) and improvement in eczema as determined by the EASI, DLQI, and VAS for pruritus at 1 week, 2 weeks, 4 weeks, and every 4 weeks thereafter in cohort 1 and at 2 weeks, 4 weeks, and every 4 weeks thereafter in cohort 2. After the last dose of medication, patients in both cohorts were asked to return for a 4-week follow-up visit.

To participate in the study, patients must have met the following inclusion criteria: age of at least 18 years at time of consent, disease severity of at least 6 on the Rajka-Langeland severity scoring system, EASI score of at least 11, and be a candidate for or previously receiving systemic therapy. In addition, patients were required to remain on a stable regimen of triamcinolone acetonide ointment, 0.1%, for 2 weeks prior to the start of the study and throughout the trial. Most patients applied the ointment twice a day 2 times a week. No other topical therapy except emollients was allowed.

Patients were excluded if they had a history of active mycobacterial infection with any species (including *Mycobacterium tuberculosis*) within 3 years prior to the screening visit, latent or incompletely treated *M tuberculosis* infection, as indicated by a positive purified protein derivative skin test. Patients were not allowed to participate in the trial if they had had at least 3 major bacterial infections resulting in hospitalization and/or requiring intravenous antibiotic treatment within the past 2 years; clinically significant abnormality on chest radiography at screening; use of any investigational medication or systemic medication within 4 weeks prior to the start of the study drug or 5 pharmacokinetic/pharmacodynamic half-lives (whichever was longer); any clinically significant abnormality on 12-lead electrocardiogram at screening; a history of congenital or acquired immunodeficiency; positive results at screening for anti-nuclear antibody, hepatitis B surface antigen or hepatitis B core antibody, or antibodies to hepatitis C; a history of human immunodeficiency virus infection; malignant disease or a history of malignant disease (except for treated [i.e., cured] basal cell skin carcinomas>3 years prior to screening); systemic corticosteroid—dependent asthma; or active infection of any type at the time of enrollment.

As an exploratory end point to potentially identify immune pathways affected by apremilast, peripheral whole blood was obtained for differential gene expression analyses at baseline and after 3 (cohort 1) and 6 (cohort 2) months of treatment to determine apremilast's potential mechanism of action in patients with atopic dermatitis. RNA isolation and microarray analyses were performed in the Oregon Health and Science University Gene Microarray Shared Resource. Total RNA was isolated from PAXGene tubes using the PAXGene Blood RNA Isolation kit (QIAGEN Inc). RNA quantity was measured by spectrophotometric analysis; RNA quality was evaluated by size analysis on the Bioanalyzer 2100 (Agilent Technologies Inc). All samples passed RNA quality assessment review.

RNA samples were labeled using the OvationWTAPico Amplification and Labeling System (NuGEN Technologies Inc). Fifty nanograms of each sample were amplified with the Ovation WTA Pico kit, converted to sense complementary DNA (cDNA) with the WT-Ovation Exon Module, version 1, kit, and labeled with the Encore Biotin Module kit. Hybridization and array processing were performed as described in the NuGEN Encore Biotin Module User Guide http://www.nugeninc.com/tasks/sites/nugen/assets/File/user_guides/userguide_encore_biotin.pdf). Two micrograms of each labeled cDNA target werehybridized with the GeneChip Human Gene 1.0 ST array (Affymetrix) and scanned on the Affymetrix GeneChip 3000 Scanner. The array image was processed with Affymetrix Command Console (version 3.1.1). Data were normalized using the robust multichip average method.

Differential expression analyses were performed on 16 paired samples. All putatively differentially expressed genes were based on false discovery rate-adjusted P values<0.05. Based on the putative differentially expressed gene list, both enriched pathways and functional gene ontologic characteristics were identified (P<0.05 for hypergeometric test) in the GoStats package within the Bioconductor statistical programming environment (http://www.bioconductor.org).

In both cohorts 1 and 2, a trend toward improvement was seen in all outcomes. Intent-to-treat analyses performed at 3 months revealed significant reduction of itch from baseline (VAS) and improvement in quality of life (DLQI) in cohort 1 (P=0.02 and P=0.003, respectively). Disease severity (EASI) and quality of life (DLQI) improved in cohort 2 (P=0.008 and P=0.01, respectively). Statistically significant clinical improvement in atopic dermatitis was noted within the first 2 weeks of study drug in cohort 2 (P=0.03). Patients experienced an average reduction in itch of 49% using a VAS, from a mean baseline of 62.3 mm to 30.5 mm in cohort 1 and a 25% reduction in cohort 2, from 45.8 mm to 32.4 mm. The EASI scores reduced an average of 19% in cohort 1 from a mean baseline of 30.9 to 22.1 and an average of 39% in cohort 2, from a mean baseline of 21.4 to 13.2 at 3 months. The DLQI scores reduced an average of 55% in cohort 1, from a mean baseline of 14.2 to 6.2 and an average of 58% in cohort 2, from a mean baseline of 10.1 to 3.8. In cohort 1, patients reported a statistically significant decline in pruritus within the first 2 weeks of use (P=0.045) with a trend for a decline in pruritus in cohort 2 (P=0.06). In cohort 1, 1 of 6 patients reduced their IGA score by 1 U (e.g., from very severe to severe). Two of 10 patients in cohort 2 reduced their IGA score by 1 U. No patient in either cohort reached an IGA score of clear or almost clear at the 3-month time point. One patient achieved an IGA score of mild in cohort 2.

Evaluation of cohort 1 was concluded at 3 months; consequently, no 6-month data were available for that cohort. Statistically significant improvement was seen in all outcomes at 6 months in cohort 2. Intent to treat analyses revealed significant reduction in EASI, from 21.1 to 11.6 (P=0.002); VAS, from 45.8 mm to 25.3 mm (P=0.03); and the DLQI, from 10.1 mm to 4.2 mm (P=0.03). Per protocol, EASI reduced from 21.1 to 10.4 (P=0.001), VAS from 45.8 to 22.7 (P=0.01), and DLQI from 10.1 to 4.0 (P=0.02). Five patients (50%) improved at least 1 U in the IGA at 6 months. Four of these 5 reached an IGA of mild, and 1 achieved an IGA of almost clear.

Post hoc intent-to-treat analyses performed on combined data from both cohorts were performed to improve the power of our analyses. The data from both cohorts combined showed statistically significant improvement in all outcomes. The EASI score was reduced from a mean baseline of 24.8 to 16.2 (P=0.002), the VAS was reduced from a mean baseline of 52.0 mm to 31.7 mm (P=0.003), and the DLQI was reduced from a mean baseline of 11.6 to 4.7 (P=0.001). Post hoc per-protocol analyses, which included data from all patients who were able to finish the study, also revealed significance in all outcomes (EASI, P=0.001; VAS, P=0.007; DLQI, P=0.001).

In cohort 1, gene expression data revealed significant differential expression of the cAMP response element binding (CREB) pathway (P=3.19×10$^4$) and BAD (bcl-2 antagonist of cell death) phosphorylation pathway (P=2.54×10$^3$). In addition, gene ontologic analyses of biological processes revealed significant differential expression of chemokine-mediated signaling (P=9.5×10$^6$), IL-12 signaling (P<0.05), cytoskeleton remodeling (P<0.05), and regulation of immune complex clearing by monocytes and macrophages (P=1.9×10$^6$). In cohort 2, there was significant differential expression of CCR3 signaling in eosinophils (P=5 0.497× 10$^2$).

5.4. Clinical Activity of Apremilast in Patients with Ankylosing Spondylitis in a Clinical Study A 24-week open-label clinical study of adult subjects with moderate to severe ankylosing spondylitis is conducted to assess the ability of an oral formulation comprising apremilast to treat patients having ankylosing spondylitis. All subjects will receive apremilast at a dose of 30 mg twice daily for a total of 24 weeks after the initial dosing schedule. The dose may be reduced to 30 mg per day if significant adverse events develop that lead to poor tolerability. After the last dose of apremilast, there will be a 4-week follow-up period. Subjects will be evaluated on Days 169 and 197.

Adult male and female subjects 18 years of age or older will participate in this study after the objectives, methods, and potential hazards of the study have been fully explained, and after they have signed the informed consent form. The Investigator is responsible for keeping a record of all subjects who sign an informed consent form for entry into this study. Screening procedures will be followed. To be enrolled into the study, subjects must meet the inclusion/exclusion criteria, which includes a diagnosis of ankylosing spondylitis.

Dose Titration Schedule:
Target Dose: 30 mg (po) BID
Day 1: 10 mg in the morning
Day 2: 10 mg BID
Day 3: 10 mg morning; 20 mg after noon
Day 4: 20 mg BID
Day 5: 20 mg morning; 30 mg after noon
Day 6 onward: 30 mg BID In certain patients, a dosing schedule with an amount up to 20 mg BID is used.

Subjects will take apremilast tablets twice daily (BID). If at any time during the study a subject encounters overt study medication-related adverse effects, dose reduction will be allowed following discussions between the subject and the investigator.

Study medication should be taken at approximately the same time every day, 12 hours apart, once in the morning and once in the after noon. If a subject reports GI side effects when taking the study medication prior to meals, the subject will be advised to switch to the postprandial dosing schedule.

5.5. Clinical Activity of Apremilast in Patients with Rheumatoid Arthritis in a Clinical Study A 24-week open-label clinical study of adult subjects with moderate to severe rheumatoid arthritis is conducted to assess the ability of an oral formulation comprising apremilast to treat patients having rheumatoid arthritis. All subjects will receive apremilast at a dose of 30 mg twice daily for a total of 24 weeks after the initial dosing schedule. The dose may be reduced to 30 mg per day if significant adverse events develop that lead to poor tolerability. After the last dose of apremilast, there will be a 4-week follow-up period. Subjects will be evaluated on Days 169 and 197.

Adult male and female subjects 18 years of age or older will participate in this study after the objectives, methods, and potential hazards of the study have been fully explained, and after they have signed the informed consent form. The Investigator is responsible for keeping a record of all subjects who sign an informed consent form for entry into this study. Screening procedures will be followed. To be enrolled into the study, subjects must meet the inclusion/exclusion criteria, which includes a diagnosis of rheumatoid arthritis.

Dose Titration Schedule:
Target Dose: 30 mg (po) BID
Day 1: 10 mg in the morning
Day 2: 10 mg BID
Day 3: 10 mg morning; 20 mg after noon
Day 4: 20 mg BID
Day 5: 20 mg morning; 30 mg after noon
Day 6 onward: 30 mg BID In certain patients, a dosing schedule with an amount up to 20 mg BID is used.

Subjects will take apremilast tablets twice daily (BID). If at any time during the study a subject encounters overt study medication-related adverse effects, dose reduction will be allowed following discussions between the subject and the investigator.

Study medication should be taken at approximately the same time every day, 12 hours apart, once in the morning and once in the after noon. If a subject reports GI side effects when taking the study medication prior to meals, the subject will be advised to switch to the postprandial dosing schedule.

5.6. Clinical Activity of Apremilast in Patients with Behcet's Disease in a Clinical Study A 24-week open-label clinical study of adult subjects with moderate to severe Behcet's disease is conducted to assess the ability of an oral formulation comprising apremilast to treat patients having Behcet's disease. All subjects will receive apremilast at a dose of 30 mg twice daily for a total of 24 weeks after the initial dosing schedule. The dose may be reduced to 30 mg per day if significant adverse events develop that lead to poor tolerability. After the last dose of apremilast, there will be a 4-week follow-up period. Subjects will be evaluated on Days 169 and 197.

Adult male and female subjects 18 years of age or older will participate in this study after the objectives, methods, and potential hazards of the study have been fully explained, and after they have signed the informed consent form. The Investigator is responsible for keeping a record of all subjects who sign an informed consent form for entry into this study. Screening procedures will be followed. To be enrolled into the study, subjects must meet the inclusion/exclusion criteria, which includes a diagnosis of Behcet's disease.

Dose Titration Schedule:
Target Dose: 30 mg (po) BID
Days 1-2: 10 mg in the morning and 10 mg after noon
Days 3-4: 20 mg in the morning and 20 mg after noon
Days 5-onwards: 30 mg in the morning and 30 mg after noon.

Other dose titration schedules described herein, for example the titration schedules for patients with psoriasis in Example 5.1, can also be used. Subjects will take apremilast tablets twice daily (BID). If at any time during the study a subject encounters overt study medication-related adverse effects, dose reduction will be allowed following discussions between the subject and the investigator.

Study medication should be taken at approximately the same time every day, 12 hours apart, once in the morning and once in the after noon. If a subject reports GI side effects when taking the study medication prior to meals, the subject will be advised to switch to the postprandial dosing schedule.

5.7. Clinical Activity of Apremilast in Patients with Ulcerative Colitis in a Clinical Study A 24-week open-label clinical study of adult subjects with moderate to severe ulcerative colitis is conducted to assess the ability of an oral formulation comprising apremilast to treat patients having ulcerative colitis. All subjects will receive apremilast at a dose of 30 mg or 40 mg twice daily for a total of 24 weeks after the initial dosing schedule. The dose may be reduced by half if significant adverse events develop that lead to poor tolerability. After the last dose of apremilast, there will be a 4-week follow-up period. Subjects will be evaluated on Days 169 and 197.

Adult male and female subjects 18 years of age or older will participate in this study after the objectives, methods, and potential hazards of the study have been fully explained, and after they have signed the informed consent form. The Investigator is responsible for keeping a record of all subjects who sign an informed consent form for entry into this study. Screening procedures will be followed. To be enrolled into the study, subjects must meet the inclusion/exclusion criteria, which includes a diagnosis of ulcerative colitis.

Dose Titration Schedule:
Target Dose: 30 mg (po) BID
Day 1: 10 mg in the morning
Day 2: 10 mg BID
Day 3: 10 mg morning; 20 mg after noon
Day 4: 20 mg BID
Day 5: 20 mg morning; 30 mg after noon
Day 6 onward: 30 mg BID
Dose Titration Schedule:
Target Dose: 40 mg (po) BID
Day 1: 10 mg in the morning
Day 2: 10 mg BID
Day 3: 10 mg morning; 20 mg after noon
Day 4: 20 mg BID
Day 5: 20 mg morning; 30 mg after noon
Day 6: 30 mg BID
Day 7: 30 mg morning; 40 mg after noon
Day 8 onward: 40 mg BID Subjects will take apremilast tablets twice daily (BID). If at any time during the study a subject encounters overt study medication-related adverse effects, dose reduction will be allowed following discussions between the subject and the investigator.

Study medication should be taken at approximately the same time every day, 12 hours apart, once in the morning and once in the after noon. If a subject reports GI side effects when taking the study medication prior to meals, the subject will be advised to switch to the postprandial dosing schedule.

All of the references cited herein are incorporated by reference in their entirety. While the methods provided herein have been described with respect to the particular embodiments, it will be apparent to those skilled in the art that various changes and modifications can be made without departing from the spirit and scope as recited by the appended claims.

The embodiments described above are intended to be merely exemplary and those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from psoriasis, the method consisting of:
    (a) administering to the patient stereomerically pure (+)-2-[1-(3-ethoxy-4-methoxyphenyl)-2-methylsulfonylethyl]-4-acetylaminoisoindoline-1,3-dione in an initial titration dosing schedule consisting of
        (i) 10 mg in the morning on the first day of administration;
        (ii) 10 mg in the morning and 10 mg after noon on the second day of administration;
        (iii) 10 mg in the morning and 20 mg after noon on the third day of administration;
        (iv) 20 mg in the morning and 20 mg after noon on the fourth day of administration;
        (v) 20 mg in the morning and 30 mg after noon on the fifth day of administration; and
    (b) on the sixth and every subsequent day, administering to the patient stereomerically pure (+)-2-[1-(3-ethoxy-4-methoxyphenyl)-2-methylsulfonylethyl]-4-acetylaminoisoindoline-1,3-dione at a dose of between about 40 mg/day and about 100 mg/day.

2. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from psoriasis, the method consisting of:
(a) administering to the patient stereomerically pure (+)-2-[1-(3-ethoxy-4-methoxyphenyl)-2-methylsulfonylethyl]-4-acetylaminoisoindoline-1,3-dione in an initial titration dosing schedule consisting of
  (i) 10 mg in the morning on the first day of administration;
  (ii) 10 mg in the morning and 10 mg after noon on the second day of administration;
  (iii) 10 mg in the morning and 20 mg after noon on the third day of administration;
  (iv) 20 mg in the morning and 20 mg after noon on the fourth day of administration;
  (v) 20 mg in the morning and 30 mg after noon on the fifth day of administration; and
(b) on the sixth and every subsequent day, administering to the patient 30 mg in the morning and 30 mg after noon of stereomerically pure (+)-2-[1-(3-ethoxy-4-methoxyphenyl)-2-methylsulfonylethyl]-4-acetylaminoisoindoline-1,3-dione.

3. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from ankylosing spondylitis, the method consisting of:
(a) administering to the patient stereomerically pure (+)-2-[1-(3-ethoxy-4-methoxyphenyl)-2-methylsulfonylethyl]-4-acetylaminoisoindoline-1,3-dione in an initial titration dosing schedule consisting of
  (i) 10 mg in the morning on the first day of administration;
  (ii) 10 mg in the morning and 10 mg after noon on the second day of administration;
  (iii) 10 mg in the morning and 20 mg after noon on the third day of administration;
  (iv) 20 mg in the morning and 20 mg after noon on the fourth day of administration;
  (v) 20 mg in the morning and 30 mg after noon on the fifth day of administration; and
(b) on the sixth and every subsequent day, administering to the patient stereomerically pure (+)-2-[1-(3-ethoxy-4-methoxyphenyl)-2-methylsulfonylethyl]-4-acetylaminoisoindoline-1,3-dione at a dose of between about 40 mg/day and about 100 mg/day.

4. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from ankylosing spondylitis, the method consisting of:
(a) administering to the patient stereomerically pure (+)-2-[1-(3-ethoxy-4-methoxyphenyl)-2-methylsulfonylethyl]-4-acetylaminoisoindoline-1,3-dione in an initial titration dosing schedule consisting of
  (i) 10 mg in the morning on the first day of administration;
  (ii) 10 mg in the morning and 10 mg after noon on the second day of administration;
  (iii) 10 mg in the morning and 20 mg after noon on the third day of administration;
  (iv) 20 mg in the morning and 20 mg after noon on the fourth day of administration;
  (v) 20 mg in the morning and 30 mg after noon on the fifth day of administration; and
(b) on the sixth and every subsequent day, administering to the patient 30 mg in the morning and 30 mg after noon of stereomerically pure (+)-2-[1-(3-ethoxy-4-methoxyphenyl)-2-methylsulfonylethyl]-4-acetylaminoisoindoline-1,3-dione.

5. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from Behcet's disease, the method consisting of:
(a) administering to the patient stereomerically pure (+)-2-[1-(3-ethoxy-4-methoxyphenyl)-2-methylsulfonylethyl]-4-acetylaminoisoindoline-1,3-dione in an initial titration dosing schedule consisting of
  (i) 10 mg in the morning on the first day of administration;
  (ii) 10 mg in the morning and 10 mg after noon on the second day of administration;
  (iii) 10 mg in the morning and 20 mg after noon on the third day of administration;
  (iv) 20 mg in the morning and 20 mg after noon on the fourth day of administration;
  (v) 20 mg in the morning and 30 mg after noon on the fifth day of administration; and
(b) on the sixth and every subsequent day, administering to the patient stereomerically pure (+)-2-[1-(3-ethoxy-4-methoxyphenyl)-2-methylsulfonylethyl]-4-acetylaminoisoindoline-1,3-dione at a dose of between about 40 mg/day and about 100 mg/day.

6. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from Behcet's disease, the method consisting of:
(a) administering to the patient stereomerically pure (+)-2-[1-(3-ethoxy-4-methoxyphenyl)-2-methylsulfonylethyl]-4-acetylaminoisoindoline-1,3-dione in an initial titration dosing schedule consisting of
  (i) 10 mg in the morning on the first day of administration;
  (ii) 10 mg in the morning and 10 mg after noon on the second day of administration;
  (iii) 10 mg in the morning and 20 mg after noon on the third day of administration;
  (iv) 20 mg in the morning and 20 mg after noon on the fourth day of administration;
  (v) 20 mg in the morning and 30 mg after noon on the fifth day of administration; and
(b) on the sixth and every subsequent day, administering to the patient 30 mg in the morning and 30 mg after noon of stereomerically pure (+)-2-[1-(3-ethoxy-4-methoxyphenyl)-2-methylsulfonylethyl]-4-acetylaminoisoindoline-1,3-dione.

7. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from rheumatoid arthritis, the method consisting of:
(a) administering to the patient stereomerically pure (+)-2-[1-(3-ethoxy-4-methoxyphenyl)-2-methylsulfonylethyl]-4-acetylaminoisoindoline-1,3-dione in an initial titration dosing schedule consisting of
  (i) 10 mg in the morning on the first day of administration;

(ii) 10 mg in the morning and 10 mg after noon on the second day of administration;
(iii) 10 mg in the morning and 20 mg after noon on the third day of administration;
(iv) 20 mg in the morning and 20 mg after noon on the fourth day of administration;
(v) 20 mg in the morning and 30 mg after noon on the fifth day of administration; and (b) on the sixth and every subsequent day, administering to the patient stereomerically pure (+)-2-[1-(3-ethoxy-4-methoxyphenyl)-2-methylsulfonylethyl]-4-acetylaminoisoindoline-1,3-dione at a dose of between about 40 mg/day and about 100 mg/day.

8. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from rheumatoid arthritis, the method consisting of:

(a) administering to the patient stereomerically pure (+)-2-[1-(3-ethoxy-4-methoxyphenyl)-2-methylsulfonylethyl]-4-acetylaminoisoindoline-1,3-dione in an initial titration dosing schedule consisting of
(i) 10 mg in the morning on the first day of administration;
(ii) 10 mg in the morning and 10 mg after noon on the second day of administration;
(iii) 10 mg in the morning and 20 mg after noon on the third day of administration;
(iv) 20 mg in the morning and 20 mg after noon on the fourth day of administration;
(v) 20 mg in the morning and 30 mg after noon on the fifth day of administration; and (b) on the sixth and every subsequent day, administering to the patient 30 mg in the morning and 30 mg after noon of stereomerically pure (+)-2-[1-(3-ethoxy-4-methoxyphenyl)-2-methylsulfonylethyl]-4-acetylaminoisoindoline-1,3-dione.

9. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from atopic dermatitis, the method consisting of:

(a) administering to the patient stereomerically pure (+)-2-[1-(3-ethoxy-4-methoxyphenyl)-2-methylsulfonylethyl]-4-acetylaminoisoindoline-1,3-dione in an initial titration dosing schedule consisting of
(i) 10 mg in the morning on the first day of administration;
(ii) 10 mg in the morning and 10 mg after noon on the second day of administration;
(iii) 10 mg in the morning and 20 mg after noon on the third day of administration;
(iv) 20 mg in the morning and 20 mg after noon on the fourth day of administration;
(v) 20 mg in the morning and 30 mg after noon on the fifth day of administration; and (b) on the sixth and every subsequent day, administering to the patient stereomerically pure (+)-2-[1-(3-ethoxy-4-methoxyphenyl)-2-methylsulfonylethyl]-4-acetylaminoisoindoline-1,3-dione at a dose of between about 40 mg/day and about 100 mg/day.

10. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from atopic dermatitis, the method consisting of:

(a) administering to the patient of stereomerically pure (+)-2-[1-(3-ethoxy-4-methoxyphenyl)-2-methylsulfonylethyl]-4-acetylaminoisoindoline-1,3-dione in an initial titration dosing schedule consisting of
(i) 10 mg in the morning on the first day of administration;
(ii) 10 mg in the morning and 10 mg after noon on the second day of administration;
(iii) 10 mg in the morning and 20 mg after noon on the third day of administration;
(iv) 20 mg in the morning and 20 mg after noon on the fourth day of administration;
(v) 20 mg in the morning and 30 mg after noon on the fifth day of administration; and (b) on the sixth and every subsequent day, administering to the patient 30 mg in the morning and 30 mg after noon of stereomerically pure (+)-2-[1-(3-ethoxy-4-methoxyphenyl)-2-methylsulfonylethyl]-4-acetylaminoisoindoline-1,3-dione.

11. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from Crohn's disease, the method consisting of:

(a) administering to the patient stereomerically pure (+)-2-[1-(3-ethoxy-4-methoxyphenyl)-2-methylsulfonylethyl]-4-acetylaminoisoindoline-1,3-dione in an initial titration dosing schedule consisting of
(i) 10 mg in the morning on the first day of administration;
(ii) 10 mg in the morning and 10 mg after noon on the second day of administration;
(iii) 10 mg in the morning and 20 mg after noon on the third day of administration;
(iv) 20 mg in the morning and 20 mg after noon on the fourth day of administration;
(v) 20 mg in the morning and 30 mg after noon on the fifth day of administration; and (b) on the sixth and every subsequent day, administering to the patient stereomerically pure (+)-2-[1-(3-ethoxy-4-methoxyphenyl)-2-methylsulfonylethyl]-4-acetylaminoisoindoline-1,3-dione at a dose of between about 40 mg/day and about 100 mg/day.

12. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from Crohn's disease, the method consisting of:

(a) administering to the patient stereomerically pure (+)-2-[1-(3-ethoxy-4-methoxyphenyl)-2-methylsulfonylethyl]-4-acetylaminoisoindoline-1,3-dione in an initial titration dosing schedule consisting of
(i) 10 mg in the morning on the first day of administration;
(ii) 10 mg in the morning and 10 mg after noon on the second day of administration;
(iii) 10 mg in the morning and 20 mg after noon on the third day of administration;
(iv) 20 mg in the morning and 20 mg after noon on the fourth day of administration;
(v) 20 mg in the morning and 30 mg after noon on the fifth day of administration; and (b) on the sixth and every subsequent day, administering to the patient 30 mg in the morning and 30 mg after noon of stereomerically pure (+)-2-[1-(3-ethoxy-4-methoxyphenyl)-2-methylsulfonylethyl]-4-acetylaminoisoindoline-1,3-dione.

13. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from ulcerative colitis, the method consisting of:
(a) administering to the patient stereomerically pure (+)-2-[1-(3-ethoxy-4-methoxyphenyl)-2-methylsulfonylethyl]-4-acetylaminoisoindoline-1,3-dione in an initial titration dosing schedule consisting of
  (i) 10 mg in the morning on the first day of administration;
  (ii) 10 mg in the morning and 10 mg after noon on the second day of administration;
  (iii) 10 mg in the morning and 20 mg after noon on the third day of administration;
  (iv) 20 mg in the morning and 20 mg after noon on the fourth day of administration;
  (v) 20 mg in the morning and 30 mg after noon on the fifth day of administration; and
(b) on the sixth and every subsequent day, administering to the patient stereomerically pure (+)-2-[1-(3-ethoxy-4-methoxyphenyl)-2-methylsulfonylethyl]-4-acetylaminoisoindoline-1,3-dione at a dose of between about 40 mg/day and about 100 mg/day.

14. A method for treating a patient with stereomerically pure (+)-2-[1-(3-ethoxy-4-methoxyphenyl)-2-methylsulfonylethyl]-4-acetylaminoisoindoline-1,3-dione, wherein the patient is suffering from ulcerative colitis, the method consisting of:
(a) administering to the patient stereomerically pure (+)-2-[1-(3-ethoxy-4-methoxyphenyl)-2-methylsulfonylethyl]-4-acetylaminoisoindoline-1,3-dione in an initial titration dosing schedule consisting of
  (i) 10 mg in the morning on the first day of administration;
  (ii) 10 mg in the morning and 10 mg after noon on the second day of administration;
  (iii) 10 mg in the morning and 20 mg after noon on the third day of administration;
  (iv) 20 mg in the morning and 20 mg after noon on the fourth day of administration;
  (v) 20 mg in the morning and 30 mg after noon on the fifth day of administration; and
(b) on the sixth and every subsequent day, administering to the patient 30 mg in the morning and 30 mg after noon of stereomerically pure (+)-2-[1-(3-ethoxy-4-methoxyphenyl)-2-methylsulfonylethyl]-4-acetylaminoisoindoline-1,3-dione.

15. A method as in any one of claims 1-14, wherein the stereomerically pure (+)-2-[1-(3-ethoxy-4-methoxyphenyl)-2-methylsulfonylethyl]-4-acetylaminoisoindoline-1,3-dione comprises greater than about 90% by weight of the (+) isomer of 2-[1-(3-ethoxy-4-methoxyphenyl)-2-methylsulfonylethyl]-4-acetylaminoisoindoline-1,3-dione based on the total weight percent of 2-[1-(3-ethoxy-4-methoxyphenyl)-2-methylsulfonylethyl]-4-acetylaminoisoindoline-1,3-dione.

16. A method as in any one of claims 1-14, wherein the stereomerically pure (+)-2-[1-(3-ethoxy-4-methoxyphenyl)-2-methylsulfonylethyl]-4-acetylaminoisoindoline-1,3-dione comprises greater than about 95% by weight of the (+) isomer of 2-[1-(3-ethoxy-4-methoxyphenyl)-2-methylsulfonylethyl]-4-acetylaminoisoindoline-1,3-dione based on the total weight percent of 2-[1-(3-ethoxy-4-methoxyphenyl)-2-methylsulfonylethyl]-4-acetylaminoisoindoline-1,3-dione.

17. A method as in any one of claims 1-14, wherein the stereomerically pure (+)-2-[1-(3-ethoxy-4-methoxyphenyl)-2-methylsulfonylethyl]-4-acetylaminoisoindoline-1,3-dione comprises greater than about 96% by weight of the (+) isomer of 2-[1-(3-ethoxy-4-methoxyphenyl)-2-methylsulfonylethyl]-4-acetylaminoisoindoline-1,3-dione based on the total weight percent of 2-[1-(3-ethoxy-4-methoxyphenyl)-2-methylsulfonylethyl]-4-acetylaminoisoindoline-1,3-dione.

18. A method as in any one of claims 1-14, wherein the stereomerically pure (+)-2-[1-(3-ethoxy-4-methoxyphenyl)-2-methylsulfonylethyl]-4-acetylaminoisoindoline-1,3-dione comprises greater than about 97% by weight of the (+) isomer of 2-[1-(3-ethoxy-4-methoxyphenyl)-2-methylsulfonylethyl]-4-acetylaminoisoindoline-1,3-dione based on the total weight percent of 2-[1-(3-ethoxy-4-methoxyphenyl)-2-methylsulfonylethyl]-4-acetylaminoisoindoline-1,3-dione.

19. A method as in any one of claims 1-14, wherein the stereomerically pure (+)-2-[1-(3-ethoxy-4-methoxyphenyl)-2-methylsulfonylethyl]-4-acetylaminoisoindoline-1,3-dione comprises greater than about 98% by weight of the (+) isomer of 2-[1-(3-ethoxy-4-methoxyphenyl)-2-methylsulfonylethyl]-4-acetylaminoisoindoline-1,3-dione based on the total weight percent of 2-[1-(3-ethoxy-4-methoxyphenyl)-2-methylsulfonylethyl]-4-acetylaminoisoindoline-1,3-dione.

20. A method as in any one of claims 1-14, wherein the stereomerically pure (+)-2-[1-(3-ethoxy-4-methoxyphenyl)-2-methylsulfonylethyl]-4-acetylaminoisoindoline-1,3-dione comprises greater than about 99% by weight of the (+) isomer of 2-[1-(3-ethoxy-4-methoxyphenyl)-2-methylsulfonylethyl]-4-acetylaminoisoindoline-1,3-dione based on the total weight percent of 2-[1-(3-ethoxy-4-methoxyphenyl)-2-methylsulfonylethyl]-4-acetylaminoisoindoline-1,3-dione.

21. A method as in any one of claims 1-14, wherein the stereomerically pure (+)-2-[1-(3-ethoxy-4-methoxyphenyl)-2-methylsulfonylethyl]-4-acetylaminoisoindoline-1,3-dione is administered in tablet form.

22. A method as in any one of claims 1-14, which comprises administering stereomerically pure (+)-2-[1-(3-ethoxy-4-m ethoxyphenyl)-2-methyl sulfonylethyl]-4-acetylaminoisoindoline-1,3-dione, substantially free of any salt, or solvate forms of (+)-2-[1-(3-ethoxy-4-methoxyphenyl)-2-methylsulfonylethyl]-4-acetylaminoisoindoline-1,3-dione.

23. A method as in any one of claims 1-14, which comprises administering a pharmaceutically acceptable salt of stereomerically pure (+)-2-[1-(3-ethoxy-4-methoxyphenyl)-2-methyl sulfonylethyl]-4-acetylaminoisoindoline-1,3-dione.

24. A method as in any one of claims 1-14, which comprises administering a pharmaceutically acceptable solvate of stereomerically pure (+)-2-[1-(3-ethoxy-4-methoxyphenyl)-2-methylsulfonylethyl]-4-acetylaminoisoindoline-1,3-dione.

* * * * *

UNITED STATES PATENT AND TRADEMARK OFFICE
CERTIFICATE OF CORRECTION

PATENT NO. : 10,092,541 B2
APPLICATION NO. : 14/826027
DATED : October 9, 2018
INVENTOR(S) : Robert Day It is certified that error appears in the above-identified patent and that said Letters Patent is hereby corrected as shown below:

In the Claims

In Claim 10, at Column 34, Line 1, replace "patient of stereomerically", with -- patient stereomerically --

In Claim 22, at Column 36, Line 44, replace "(+)-2-[1-(3-ethoxy-4-m ethoxyphenyl)-2-methyl sulfonylethyl]-4-acetylaminoisoindoline-1,3-dione", with -- (+)-2-[1-(3-ethoxy-4-methoxyphenyl)-2-methylsulfonylethyl]-4-acetylaminoisoindoline-1,3-dione --

In Claim 23, at Column 36, Line 52, replace "(+)-2-[1-(3-ethoxy-4-methoxyphenyl)-2-methyl sulfonylethyl]-4-acetylaminoisoindoline-1,3-dione", with -- (+)-2-[1-(3-ethoxy-4-methoxyphenyl)-2-methylsulfonylethyl]-4-acetylaminoisoindoline-1,3-dione --

Signed and Sealed this
Eleventh Day of December, 2018

Andrei Iancu
*Director of the United States Patent and Trademark Office*